US011026934B2

(12) United States Patent
Kandavilli et al.

(10) Patent No.: US 11,026,934 B2
(45) Date of Patent: *Jun. 8, 2021

(54) TOPICAL RETINOID COMPOSITIONS

(71) Applicant: DR. REDDY'S LABORATORIES LTD., Telangana (IN)

(72) Inventors: Sateesh Kandavilli, Plainsboro, NJ (US); Franklin Okumu, Morristown, NJ (US); Manish M. Bankar, Maharashtra (IN); Sujit Kumar Dolai, Odisha (IN)

(73) Assignee: DR. REDDY'S LABORATORIES LTD., Telangana (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/369,320

(22) Filed: Mar. 29, 2019

(65) Prior Publication Data

US 2019/0224181 A1 Jul. 25, 2019

Related U.S. Application Data

(63) Continuation of application No. 15/902,635, filed on Feb. 22, 2018, now Pat. No. 10,716,781, which is a
(Continued)

(51) Int. Cl.
*A61K 31/4436* (2006.01)
*A61K 8/67* (2006.01)
(Continued)

(52) U.S. Cl.
CPC .......... *A61K 31/4436* (2013.01); *A61C 19/00* (2013.01); *A61C 19/08* (2013.01);
(Continued)

(58) Field of Classification Search
None
See application file for complete search history.

(56) References Cited

U.S. PATENT DOCUMENTS 3,965,275 A * 6/1976 Hidy .................... A61K 31/365
514/450
4,154,823 A * 5/1979 Schutt .................... A61Q 17/04
424/734
(Continued)

FOREIGN PATENT DOCUMENTS

JP   H10-226634 A    8/1998
JP   2007-508243 A   4/2007
(Continued)

OTHER PUBLICATIONS

Convergent Cosmetics, accessed May 9, 2019 (Year: 2019).*
(Continued)

*Primary Examiner* — Melissa S Mercier
(74) *Attorney, Agent, or Firm* — Stites & Harbison, PLLC; Mandy Wilson Decker; Sean P. Ritchie

(57) ABSTRACT

The present application relates to topical compositions. In particular, the present application relates to a topical composition comprising retinoid as active agent, and pharmaceutically acceptable excipient(s), and a process of preparing such compositions. Further, the present application relates to method of using topical compositions for the treatment of skin disorders such as acne, rosacea, psoriasis etc.

41 Claims, 3 Drawing Sheets

Related U.S. Application Data continuation of application No. 15/621,325, filed on Jun. 13, 2017, now Pat. No. 9,931,328, which is a continuation of application No. 15/209,716, filed on Jul. 13, 2016, now Pat. No. 9,707,216.

(60) Provisional application No. 62/191,937, filed on Jul. 13, 2015.

(51) Int. Cl.

| | |
|---|---|
| A61K 9/00 | (2006.01) |
| A61K 8/49 | (2006.01) |
| A61Q 19/00 | (2006.01) |
| A61Q 19/02 | (2006.01) |
| A61Q 19/08 | (2006.01) |
| A61Q 19/10 | (2006.01) |
| A61P 17/10 | (2006.01) |
| A61P 17/00 | (2006.01) |
| A61K 31/7004 | (2006.01) |
| A61K 9/12 | (2006.01) |
| A61C 19/00 | (2006.01) |
| A61C 19/08 | (2006.01) |
| A61K 31/355 | (2006.01) |

(52) U.S. Cl.
CPC ............... *A61K 8/49* (2013.01); *A61K 8/671* (2013.01); *A61K 8/678* (2013.01); *A61K 9/0014* (2013.01); *A61K 9/122* (2013.01); *A61K 31/355* (2013.01); *A61K 31/7004* (2013.01); *A61P 17/00* (2018.01); *A61P 17/10* (2018.01); *A61Q 19/00* (2013.01); *A61Q 19/02* (2013.01); *A61Q 19/08* (2013.01); *A61Q 19/10* (2013.01); *A61K 8/498* (2013.01)

(56) References Cited

U.S. PATENT DOCUMENTS

| | | | |
|---|---|---|---|
| 4,293,542 A * | 10/1981 | Lang | A61Q 17/04 424/47 |
| 5,855,893 A | 1/1999 | Weinkauf et al. | |
| 6,338,855 B1 | 1/2002 | Albacarys et al. | |
| 6,385,623 B1 * | 5/2002 | Smith | G06F 16/178 |
| 6,495,602 B1 * | 12/2002 | Bhagwat | A61K 8/19 424/401 |
| 6,517,847 B2 | 2/2003 | Dow et al. | |
| 7,169,401 B2 * | 1/2007 | Puglia | A61K 8/37 424/401 |
| 9,707,216 B2 * | 7/2017 | Kandavilli | A61Q 19/10 |
| 9,931,328 B2 * | 4/2018 | Kandavilli | A61K 31/355 |
| 2009/0012172 A1 | 1/2009 | Fredon et al. | |
| 2010/0221194 A1 | 9/2010 | Loupenok | |
| 2016/0367570 A1 * | 12/2016 | Dow | A61K 45/06 |

FOREIGN PATENT DOCUMENTS

| | | |
|---|---|---|
| WO | 9943296 A2 | 9/1999 |
| WO | 2005/011567 A2 | 2/2005 |
| WO | 2010096868 A1 | 9/2010 |

OTHER PUBLICATIONS

Premjeet et al. (Additives in Topical Dosage Forms, International Journal of Pharmaceutical, Chemical and Biological Sciences, IJPCBS 2012, 2 (1), 78-96). (Year: 2012).*

Refina, Visocity Guide for Paints, Petroleum, and food products, accessed online Sep. 2, 2020. (Year: 2020).*

Menaa (Emulsions systems for Skin Care: from Macro to Nano-formulations, Journal of Pharmaceutical Care and Health Systems, 2014). (Year: 2014).*

Japan Patent Office, Office Action (Notice of Reasons for Refusal) issued in corresponding Application No. 2018-501272, dated Jul. 23, 2019.

The Korean Intellectual Property Office, Office Action (Notice of Rejection) issued in corresponding Application No. 10-2018-7003169, dated Sep. 27, 2019.

IP Australia, Examination Report No. 2 issued in corresponding Application No. 2016294504, dated Apr. 26, 2019.

\* cited by examiner

TOPICAL RETINOID COMPOSITIONS

RELATED APPLICATIONS

This application is a continuation of U.S. patent application Ser. No. 15/902,635, filed Feb. 22, 2018, which claims priority to U.S. patent application Ser. No. 15/621,325, filed Jun. 13, 2017, now issued as U.S. Pat. No. 9,931,328, which claims priority to U.S. patent application Ser. No. 15/209,716, filed Jul. 13, 2016, now issued as U.S. Pat. No. 9,707,216, which claims priority from U.S. Provisional Application Ser. No. 62/191,937, filed Jul. 13, 2015, the entire disclosures of which are incorporated herein by this reference.

FIELD OF THE INVENTION

The present application relates to a retinoid-containing topical composition.

BACKGROUND

Retinoid compounds are often used in the treatment of various skin disorders such as acne, psoriasis and like and are available both as naturally-occurring and synthetic derivatives. The naturally-occurring retinoid(s) are derived from Vitamin A; examples are tretinoin (all trans retinoic acid), retinol, retinal and the like. The synthetic retinoid(s) are small chemical molecules that act on retinoic acid receptors (RARs) like naturally occurring retinoid(s); examples of synthetic derivatives are acitretin, tazarotene, and adapalene and the like.

Tretinoin (Formula I) is one of the naturally-occurring retinoids, and is also known as "all trans retinoic acid". Tretinoin is approved worldwide in topical dosage forms such as gel, cream and the like, for the treatment of acne vulgaris.

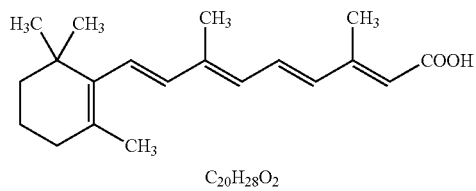

Formula I $C_{20}H_{28}O_2$

Tazarotene (Formula II) is a synthetic derivative, which acts on retinoic acid receptors (RARs) and is a prodrug that is converted into its active form, tazarotenic acid, by rapid deesterification.

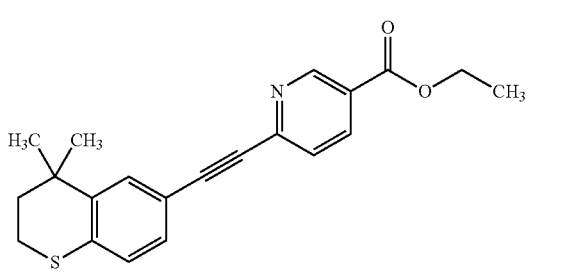

Formula II

These retinoids are widely used in various topical dosage forms having the advantage of the ease of their administration to the target site. Generally, skin disorders such as acne are treated by the topical administration of active compounds.

Acne vulgaris is one of the common skin disorders that affect the skin's oil glands. The small holes in the skin (pores) connect to oil glands under the skin. These glands make an oily substance called sebum. Pores of the skin are connected to the glands through a canal called a follicle. Acne is thought to be caused by multiple factors such as overproduction of oil in the skin called sebum, which is increased under the influence of hormones. When the follicle of a skin gland clogs up, it causes inflammation, and thus a pimple grows. Acne affects 85-100% of people at some point in their lives. The most common acne locations include face, neck, chest, and back, where most of the sebaceous glands are located resulting in psychological and social problems.

The currently-available compositions for treating acne include 1) Topical tretinoin; 2) Topical clindamycin alone or in combination with tretinoin and benzoyl peroxide; 3) Oral minocycline; 4) Topical adapalene; 5) Topical tazarotene; 6) Topical benzoyl peroxide alone or in combination with other drugs, and more. Topical retinoid treatment is a promising therapy for the treatment of acne; however the main shortcoming in topical retinoids is that they may cause irritation at the site of administration. Long term application of topical retinoids to the patient's skin causes local irritation.

Generally, topical wash compositions have a profound effect in acne treatment. The cleansing effects of these compositions involve eliminating dirt and dead cells, clearing up acne blemishes and black heads, and preventing the development of new acne pimples. The ideal skin wash composition removes surface oils derived from sebaceous glands, and associated debris, without affecting natural constitutive lipids of skin. Most of the detergent-/soap-containing skin-cleansing compositions have the tendency to affect the natural lipid structure of the skin, or cause dryness to the skin, and some of the facial wash compositions cause greasy feel to the skin. On the other hand, therapeutic retinoids cause irritation to the patient's skin. These skin-cleansing compositions are being offered either as clear liquids, or as opaque base creams and gels.

U.S. Pat. No. 7,465,461 discloses a method of enhancing moisture or reducing dryness using wet skin treatment composition that leaves the skin feeling clean, but non-greasy.

U.S. Pat. No. 6,017,938 discloses a method of treating acne using short-term contact with an acetylenic retinoid, preferably tazarotene and related compounds.

U.S. Pat. No. 6,048,902 discloses a method of treating psoriasis by short-term contact of a topically-applied retinoid composition.

US patent application 2010/0098776 discloses soap-based liquid body and facial wash compositions comprising an antimicrobial agent. Soap-based liquid composition enhances antimicrobial deposition in the skin.

It is found that the topical composition of the present application comprising a retinoid compound improves skin disorders such as acne or psoriasis by alleviating both inflamed and non-inflamed lesions and the administration of this composition provides more retinoid deposition and less irritation to the subject's skin. The composition also possesses cleansing property without causing dryness to the skin thus, providing better patient compliance. The topical compositions of the present application are topical wash compositions.

SUMMARY OF THE INVENTION

An aspect of the present application relates to a retinoid-containing topical composition.

Another aspect of the present application relates to a topical composition comprising: a) a retinoid compound; b) at least one foaming agent; c) at least one anti-irritant; and d) one or more dermatologically acceptable excipient(s).

Another aspect of the present application relates to a topical composition comprising: a) tazarotene; b) at least one foaming agent; c) at least one anti-irritant; and d) one or more dermatologically acceptable excipients.

Another aspect of the present application relates to a topical composition comprising a) tazarotene; b) at least one foaming agent; c) at least one anti-irritant; and d) one or more dermatologically acceptable excipients; wherein said composition is applied to the affected area of skin and rinsed off within about 15 minutes; and provides an effective skin deposition of retinoid compound(s) with less irritation.

Yet another aspect of the present application relates to a method of administering a retinoid-containing topical composition for the treatment of skin disorders such as acne, rosacea, psoriasis, atopic dermatitis and the like.

Yet another aspect of the present application relates to a method of administering a tazarotene containing topical composition for the treatment of skin disorders such as acne, rosacea, psoriasis, atopic dermatitis and the like.

In another aspect, the topical compositions of the present application are topical wash compositions.

BRIEF DESCRIPTION OF THE DRAWING

FIG. 4A shows Formula III—Methyl 6-[(4,4-dimethyl-3,4-dihydro-2Hthiochromen-6-yl) ethynyl]nicotinate (Impurity A). FIG. 4B shows Formula IV—Ethyl 6-[(4,4-dimethyl-1-oxido-3,4-dihydro-2H-thiochromen-6-yl) ethynyl]nicotinate (Impurity B). FIG. 4C shows 6-[(4,4-dimethyl-3,4-dihydro-2H-thiochromen-6-yl)ethynyl]nicotinic acid (Impurity C).

DESCRIPTION OF EXEMPLARY EMBODIMENTS

Figure 1:
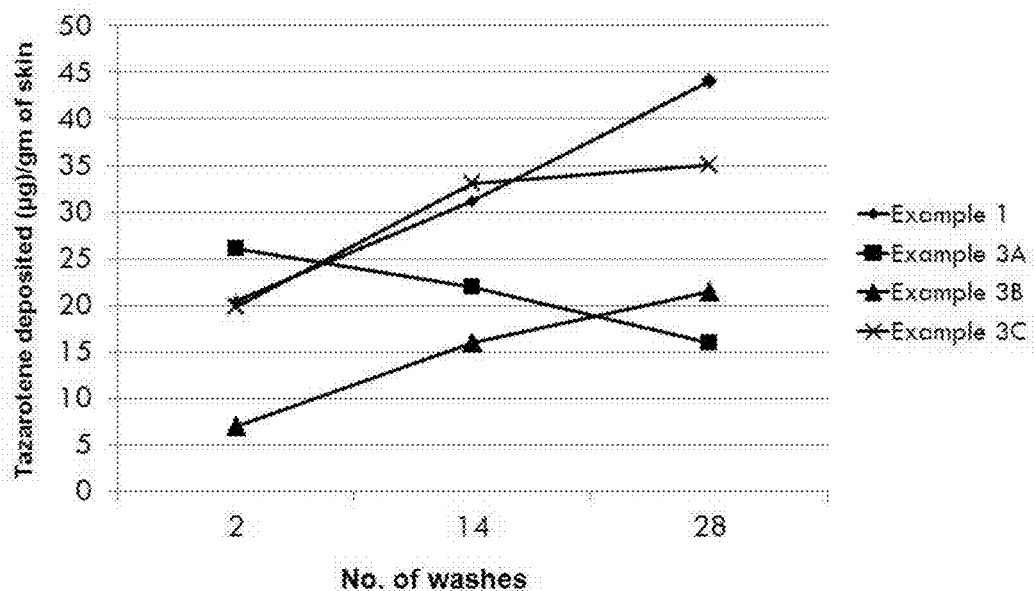
FIG. 1 is a graph showing the effect of number of washes on cumulative tazarotene deposition in rat skin.
Figure 2:
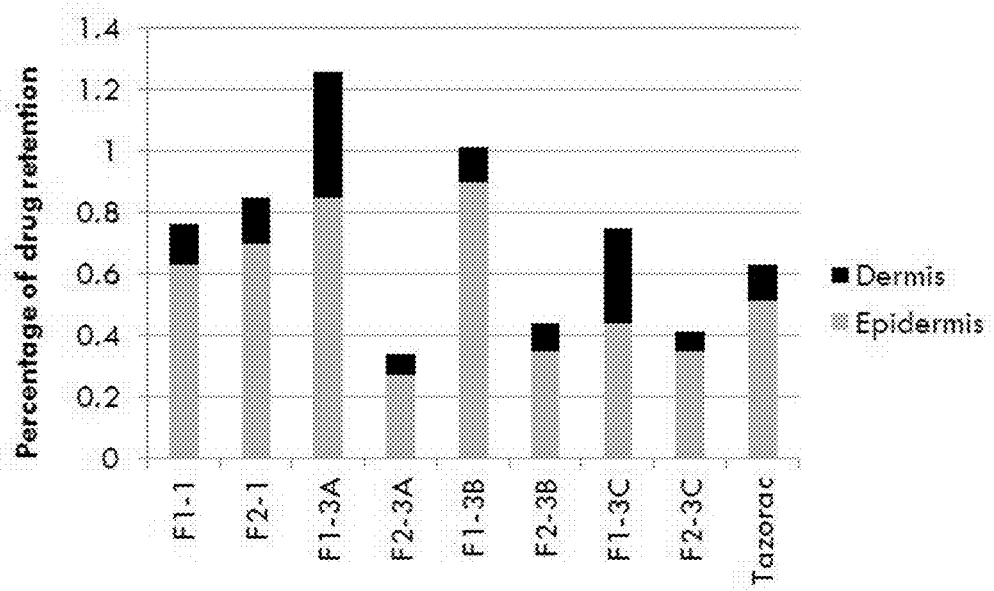
FIG. 2 is a graph showing the percentage of skin retention of tazarotene in neonatal minipigs skin.
Figure 3:
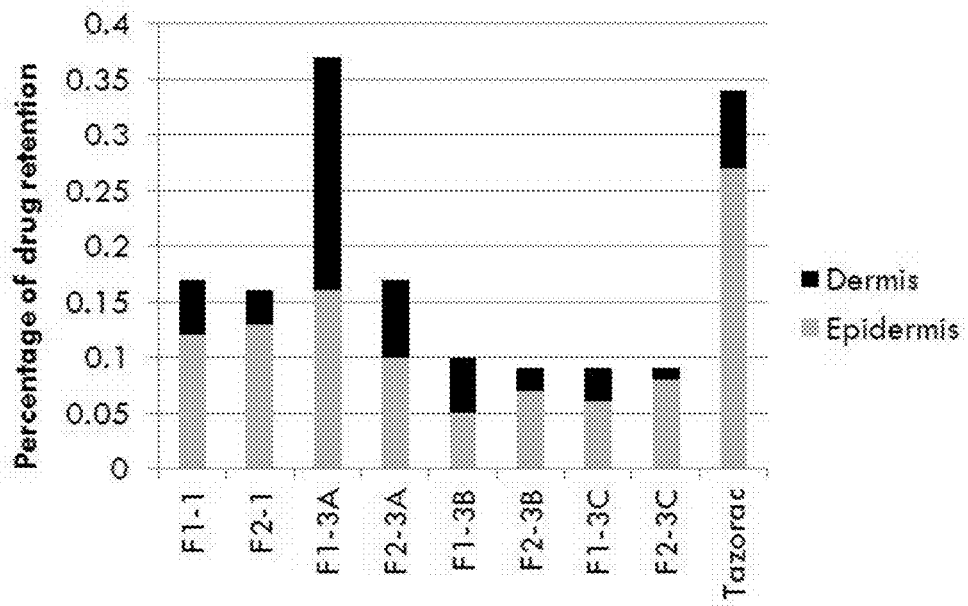
FIG. 3 is a graph showing the percentage of skin retention of tazarotenic acid in neonatal minipigs skin.
Figure 4A:
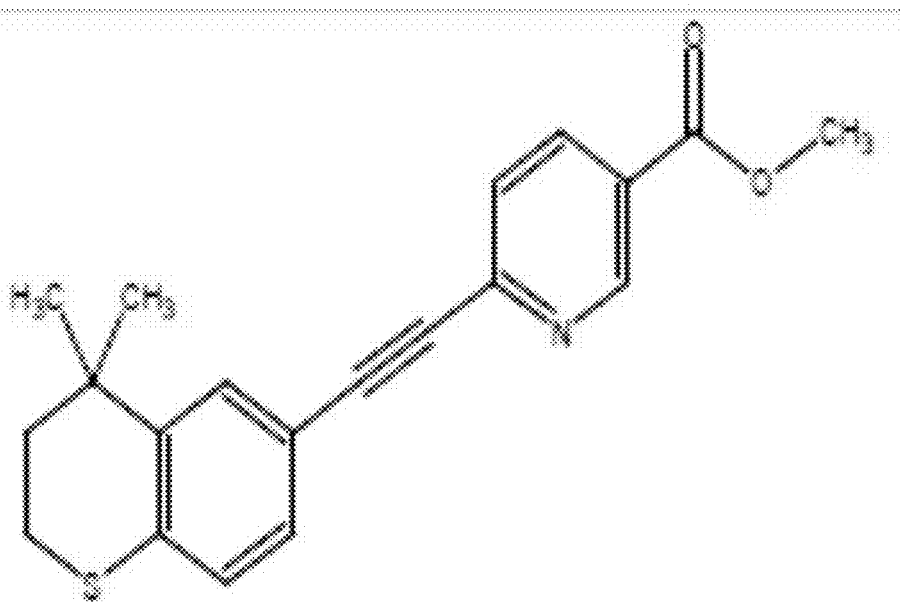
FIGS. 4A-C show the structures of related substances of tazarotene.
Figure 4B:
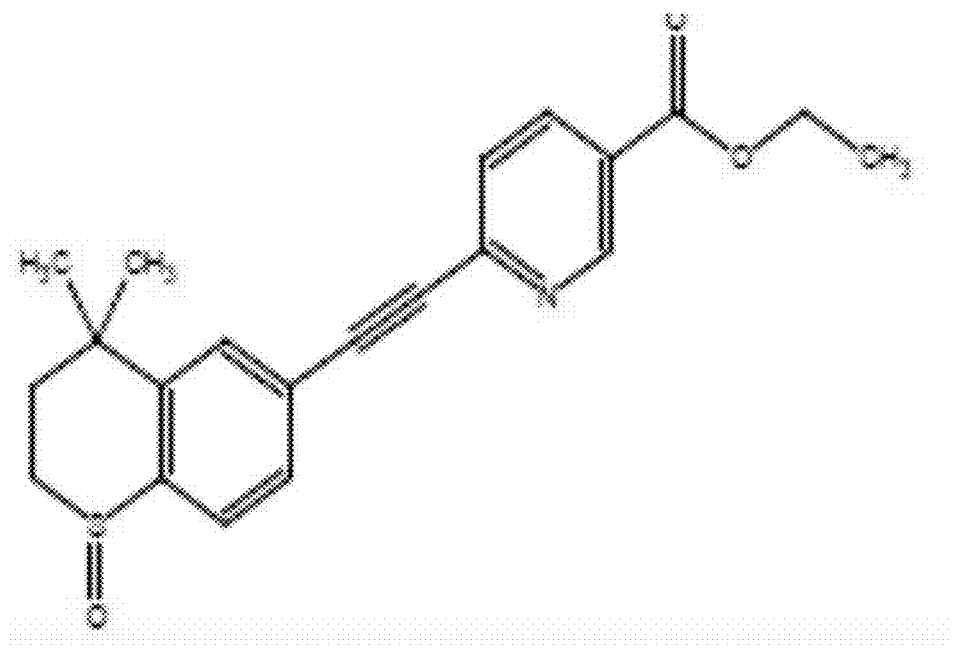
Figure 4C:
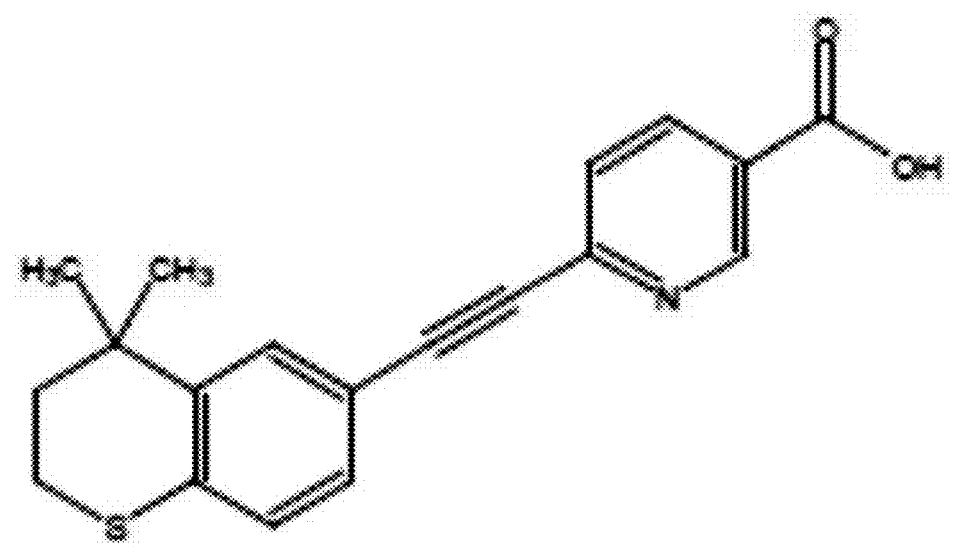

The terms "topical composition," "topical formulation," "topical wash composition," or such variants are used interchangeably in the present application to denote the composition comprising retinoid compound, especially tazarotene meant for topical application. In some embodiments, as described in detail below, the topical composition may tend to form foam at application site by manual act such as rubbing or massaging, or applying physical pressure or mechanical device assistance.

The term "topical wash," as used herein, refers to a composition having liquid to a gel-like consistency. This term may be interchangeably used with "skin cleansing composition", "face wash composition" or "body wash composition", that are useful for cleansing or rinsing the skin (face, hair or body) for the treatment of affected skin regions.

The term "pH balanced", as used herein, refers to a composition having pH from about 4 to about 7.

The terms "applying," "administering," or "administration," as used herein, refer to topical application of a retinoid-containing topical composition to affected and adjoining areas of skin by spreading or gentle rubbing or massaging. The composition is rinsed off immediately after application without allowing an extended contact after application.

The terms "retinoid compound" or "retinoid," as used herein, refer to any naturally occurring or synthetic derivatives, selected from tretinoin, tazarotene, tazarotenic acid, adapalene, isotretinoin, and acitretin. The above active agent may be administered in the form of its pharmaceutically acceptable salts, esters, isomers, enantiomers, active metabolites, and/or prodrugs thereof as well.

The term "skin disorder(s)," as used herein, refers to any inflammatory skin disorder selected from acne vulgaris, psoriasis, rosacea, atopic dermatitis, skin wrinkles, facial mottle, hyperpigmentation, hypopigmentation, photoaging, papule, pustule, nodulocystic acne lesion (both inflamed and non-inflamed), and lentigo.

As used herein, the term "about," when referring to a value, or to an amount of mass, weight, time, volume, concentration or percentage, is meant to encompass variations of, in some aspects, ±20%, in some aspects, ±10%, in some aspects, ±5%, in some aspects, ±1%, in some aspects ±0.5%, and in some aspects, ±0.1% of the specified amount, as such variations are appropriate to perform the disclosed method.

The term "aqueous based composition," as used herein, refers to a composition having a percentage of water in the composition that is at least about 50% w/w of the final weight of the composition. In some embodiments, the aqueous-based topical composition herein refers to a composition comprising at least about 60% w/w of water based on the final weight of the composition, or comprising at least about 70% w/w of water based on the final weight of the composition, or comprising at least about 80% w/w of water based on the final weight of the composition. The aqueous-based retinoid-containing topical composition provides a natural feel, non-greasy, no dryness and less irritation to the skin.

The terms "active," "active agent," or "active substance," as used herein, refer primarily to retinoid compounds. In some aspects, these terms refer to an active agent other than a retinoid compound selected from group comprising of: anti-bacterial, corticosteroids, antimicrobials, anti-leprosy drugs, immunomodulators, anti-inflammatory agents and/or combination thereof. In a specific aspect, the one or more active agent(s) are selected from betamethasone, halobetasol, clobetasol, clofazimine, azelaic acid, dapsone or combination thereof.

An aspect of the present application relates to a topical composition comprising: a) a retinoid compound; b) at least one foaming agent; c) at least one anti-irritant; and d) one or more dermatologically acceptable excipient(s).

An aspect of the present application relates to a topical composition comprising a) a retinoid compound; b) at least one foaming agent; c) at least one anti-irritant; and d) one or more dermatologically acceptable excipients; wherein said composition is applied to the affected area of skin and rinsed off within about 15 minutes; and provides effective skin deposition of retinoid compound(s) with less irritation than known retinoid treatments.

In another aspect, the topical compositions of the present application are topical wash compositions.

In an aspect, the present application relates to a method of administering retinoid containing topical composition comprising spreading, gentle rubbing or massaging, and allowing the composition to remain in the affected area for a minimum period of time from about 0 seconds to about 0.5, 1, 2, 3, 4, 5, 6, 7, 8, 9, 10, 11, 12, 13, 14, or 15 minutes, and rinsing off from the affected area of skin. Said minimum period of time is less than about 15 minutes, or less than about 10 minutes, or less than about 5 minutes.

In one aspect of the present application, the retinoid compound is selected from tretinoin, tazarotene, tazarotenic acid, adapalene, isotretinoin or acitretin.

In another aspect of the present application, the retinoid compound is a mixture of any of the above-identified compounds.

In another aspect of the present application, the retinoid compound is selected from tazarotenic acid, tazarotene or tretinoin.

In another aspect of the present application, the retinoid compound is tazarotene.

In another aspect of the present application, the retinoid-containing topical composition is foamable.

In another aspect of the present application, the retinoid compound is micronized.

In another aspect of the present application, the retinoid compound is in a suspended form in the topical composition.

In another aspect of the present application, the retinoid compound is solubilized in a topical composition.

Another aspect of the present application relates to a topical composition comprising: a) a retinoid compound; b) at least one foaming agent; c) at least one anti-irritant; and d) one or more dermatologically acceptable excipients, wherein the at least one active agent is other than retinoid compound(s).

Another aspect of the present application relates to an aqueous-based topical composition comprising: a) a retinoid compound; b) at least one foaming agent; c) at least one anti-irritant; and d) one or more dermatologically acceptable excipients, wherein the topical composition contains at least about 50, 55, 60, 65, 70, 75, or 80% w/w of water based on the total weight of the composition.

Another aspect of the present application relates to a retinoid-containing topical composition comprising a foaming agent in the range from about 0.01% w/w to about 10% w/w of the total weight of the composition. In some embodiments, present application relates to a retinoid-containing topical composition comprising a foaming agent at least about 0.01, 0.1, 1.0, 2.0, 3.0, 4.0, 5.0, 6.0, 7.0, 8.0, 9.0, or 10% w/w of total weight of the composition.

In an aspect of the present application, the foaming agent is selected from anionic, cationic, nonionic and amphoteric surfactants.

An aspect of the present application relates to a retinoid-containing topical composition comprising one or more dermatologically acceptable excipients selected from stabilizers, fatty alcohols, emollients, fatty acid esters, polymers, chelating agents, alpha hydroxyl acids, anti-irritants, moisturizing agents, gelling agents, foaming agents, preservatives, colorants, antioxidants and pH adjusting agents.

In an aspect, the present application relates to a retinoid-containing topical composition which is pH balanced.

In an aspect, the viscosities of retinoid-containing topical composition comprising retinoid, frequently vary in from about 100 cps to about 1,00,000 cps, or from about 1000 cps to about 80,000 cps, or from about 1000 cps to about 50,000 cps, when measured by Brookfield DV-II pro Viscometer with low viscosity spindle no. 4 at 20 rpm, and the another range of viscosity is from about 40,000 cps to about 1,00, 000 cps when measured by Brookfield DV-II pro Viscometer with low viscosity spindle no. 4 at 5 rpm.

An aspect of the present application relates to a topical composition comprising: a) a retinoid compound; b) at least one foaming agent; c) at least one anti-irritant; and d) one or more dermatologically acceptable excipients, wherein said at least one anti-irritant is polyhydroxy acid or tocofersolan.

An aspect of the present application relates to the use of a polyhydroxy acid in the retinoid-containing topical composition, as an anti-irritant. The polyhydroxy acid is present in the range from about 0.01% w/w to about 0.1, 1, 2, or 3% w/w, or from about 0.01, 0.1, 1, or 2% w/w to about 3% w/w, of the total weight of the composition and is selected from the groups consisting of: gluconic acid lactone and aldonic acid lactones such as allonolactone, altronolactone, gluconolactone, mannolactone, gulonolactone, idonolactone, galactonolactone, and talonolactone.

An aspect of the present application relates to using of the combination of anti-irritants in the retinoid-containing topical composition comprising gluconolactone and tocofersolan.

Another aspect of the present application relates to a method of administering the retinoid-containing topical composition to a patient comprising: a) shaking the composition; b) topically applying the composition to the affected area of the skin for a period of about 0 seconds to about 0.5, 1, 2, 3, 4, 5, 6, 7, 8, 9, 10, 11, 12, 13, 14, or 15 minutes; and c) rinsing off said composition from the affected area with water or suitable solvent, wherein said method deposits retinoid in the affected area of the skin. Said minimum period of time is less than about 15 minutes, or less than about 10 minutes, or less than about 5 minutes.

In an aspect, the present application relates to administering retinoid containing topical composition to the affected areas of a patient including, but not limited to, face, neck, upper chest, back, or any areas of the skin with the densest population of sebaceous follicles.

In an aspect, the present application relates to a method of treating skin disorders using retinoid-containing topical composition.

Another aspect of the present application relates to a method of treating skin disorders by administering a topical composition comprising: a) a retinoid compound; b) at least one foaming agent; c) at least one anti-irritant; and d) one or more dermatologically acceptable excipients.

In an aspect of the present application, the skin disorder is selected from acne, rosacea, psoriasis, atopic dermatitis, skin wrinkles, facial mottle, hyperpigmentation, hypopigmentation, photo aging papule, pustule, nodulocystic acne lesion (both inflamed and non-inflamed) and lentigo.

Another aspect of the present application relates to a method of treating skin disorders by administering a topical composition comprising: a) tazarotene; b) at least one foaming agent; c) at least one anti-irritant; and d) one or more dermatologically acceptable excipients, wherein the skin disorder is selected from acne, rosacea, psoriasis, atopic dermatitis, skin wrinkles, facial mottle, hyperpigmentation, hypopigmentation, photo aging papule, pustule, nodulocystic acne lesion (both inflamed and non-inflamed) and lentigo.

In a specific aspect, the present application relates to a method of treating acne by administering a topical composition comprising: a) tazarotene; b) at least one foaming agent; c) at least one anti-irritant; and d) one or more dermatologically acceptable excipients, wherein said composition is applied to the affected area of the skin and rinsed off within about 15 minutes; and provides an effective skin deposition of tazarotene with less irritation.

In a specific aspect, the present application relates to a method of treating psoriasis by administering a topical composition comprising: a) tazarotene; b) at least one foaming agent; c) at least one anti-irritant; and d) one or more dermatologically acceptable excipients, wherein said composition is applied to the affected area of skin and rinsed off within about 15 minutes; and provides an effective skin deposition of tazarotene with less irritation.

In an aspect, the present application relates to an aqueous-based topical composition comprising: a) a retinoid compound; b) at least one foaming agent; c) at least one anti-irritant; and d) one or more dermatologically acceptable agent(s), wherein said retinoid compound is selected from tazarotene, tretinoin, and adapalene.

In an aspect, the present application relates to an aqueous-based topical composition comprising: a) a retinoid compound; b) at least one foaming agent selected from disodium laureth sulfosuccinate, cocobetaine, sodium lauryl sarcosinate, and sodium lauryl sulfate; c) at least one anti-irritant is selected from polyhydroxy acids; and d) one or more dermatologically acceptable excipients selected from emollients, antioxidants, solubilizers, viscosity modifiers, stabilizers, pH adjusting agents, preservatives, fatty alcohols, fatty acid esters and polymers, and moisturizers, wherein said composition comprises at least about 60% w/w water based on the final weight of the composition.

In an aspect, the present application relates to an aqueous-based topical composition comprising: a) from about 0.01% w/w to about 1% w/w of tazarotene or pharmaceutically acceptable salt, esters thereof; b) from about 0.1% w/w to about 7% w/w of foaming agents selected from disodium laureth sulfosuccinate, cocobetaine, sodium lauryl sarcosinate, and sodium lauryl sulfate, or mixtures thereof; c) from about 0.01% w/w to about 3% w/w of at least one anti-irritant selected from polyhydroxy acids and tocofersolan, or mixtures thereof; and d) one or more dermatologically acceptable excipients selected from emollients, antioxidants, stabilizers, pH adjusting agents, preservatives, fatty alcohols, fatty acid esters and polymers, and moisturizers, wherein said composition comprises at least about 60% w/w water based on the final weight of the composition.

In an aspect, the retinoid-containing topical composition of the present application relates to a skin-cleansing composition to wash off debris, oily substances, sebum, and dead cells from the affected area of the skin, and the retinoid-containing topical composition can be applied on the affected area of skin and rinsed off within from about 0 seconds to about 15 minutes, and said composition comprises a) one or more retinoid(s); b) at least one anti-irritant; and c) one or more dermatologically acceptable excipients; wherein the composition provides therapeutically effective amount of retinoid retention in the skin with less irritation.

In another aspect, the retinoid-containing topical composition of the present application relates to a skin-cleansing composition to wash off debris, oily substances, sebum, and dead cells from the affected area of the skin, and the retinoid-containing topical composition can be applied on the affected area of skin and rinsed off within from about 0 seconds to about 15 minutes, and said composition comprises a) tazarotene; b) at least one anti-irritant; and c) one or more dermatologically acceptable excipients; wherein the composition provides therapeutically effective amount of retinoid retention in the skin with less irritation.

In an aspect, the topical composition of the present application comprises: a) tazarotene; b) at least one anti-irritant; and c) one or more dermatologically acceptable excipients; wherein said composition is rinsed off within from about 0 seconds to about 15 minutes; further providing skin cleansing effect, by washing off debris, oily substances, sebum, and dead cells from the affected area of the skin, and retention of therapeutically effective amount of retinoid in the skin with less irritation.

In some embodiments, the retinoid-containing topical composition of the present application has more skin affinity thereby exhibiting more deposition of retinoid(s) in the skin. Additionally or alternatively, in some embodiments, the retinoid compound(s) of the present application is suspended in the composition, wherein the composition is oil-in-water or water-in-oil emulsion.

In one aspect, the retinoid compound(s) in the topical composition are deposited and entrapped in the pores of the skin upon application of the topical composition. In another aspect, these deposited retinoid compounds are not washed off by the subsequent washes, and tend to release the drug even after washing.

An aspect of the present application relates to a retinoid-containing topical composition comprising water from about 30, 35, 40, 45, 50, 55, 60, 65, 70, 75, 80, 85, or 90% w/w to about 95% w/w based on the total weight of the composition. Another aspect of the present application relates to a retinoid-containing topical composition comprising water from about 30% w/w to about 35, 40, 45, 50, 55, 60, 65, 70, 75, 80, 85, or 90% w/w based on the total weight of the composition.

Another aspect of the present application relates to a retinoid-containing topical composition comprising water from about 50% w/w to about 90% w/w based on the total weight of the composition.

In certain embodiments, particle size of the retinoid compound(s) is one of the critical aspects of the present application. Lesser particle size of the retinoid compound(s) tends to show more skin deposition/retention. However, the extent of deposition of retinoid compound(s) also depends on the nature of the composition.

The cleansing effect of a retinoid-containing topical composition is optimized. If cleansing effect of the retinoid-containing topical composition is high, the drug deposition could to be low due to dislodging of previously deposited drug. In embodiments described in the present application, the drug deposition was found to increase linearly with the increasing number of washes, whereas in some compositions the initial deposition of drug decreased continuously with increasing number of washes. It has been found that the net deposition of drug in the skin is a function of cleansing effect of the composition that is optimized to maintain the effective level of the drug in patient skin.

The skin affinity exhibited by the composition establishes that the topical composition of the present application deposits retinoid compound in the skin regardless of its particle size.

An aspect of the present application relates to a retinoid-containing topical composition comprising one or more dermatologically acceptable excipients selected from stabilizers, solubilizers, solvents, anti-irritants, fatty alcohols, emollients, fatty acid esters, polymers, chelating agents, alpha hydroxyl acids, polyhydroxy acids, moisturizing agents, gelling agents, foaming agents, preservatives, colorants, antioxidants and pH adjusting agents.

In an aspect, a retinoid containing topical composition of the present application may be in the form of lotion, gel, cream, suspension, foam, soap or spray.

In an aspect, the retinoid containing topical composition of the present application may be in the form of a lotion.

According to one or more of the embodiments disclosed herein, the retinoid compound(s) are used in the present application from about 0.001% w/w to about 0.01, 0.1, 1, 2, 3, 4, or 5% w/w, from about 0.001, 0.01, 0.1, 1, 2, 3, or 4% w/w to about 5% w/w, based on total weight of the composition. In an aspect, the present application comprises retinoid compound(s) from about 0.01% w/w to about 0.1% w/w based of total weight of the composition. In an aspect, the present application comprises retinoid compound(s) at least about 0.1% w/w based of total weight of the composition.

The topical retinoid compositions available in the market are generally applied once daily before bedtime and these compositions are left on the skin for a long period of time that causes significant irritation to the patient's skin. Due to the chemical nature of retinoid compounds, topical composition containing a retinoid compound tends to show skin-irritation, and it is well documented in the state-of-art, and also it has been observed that skin-irritation caused by retinoid compounds is directly correlating with their efficacy. Lesser concentration of retinoid compound(s) shows lesser efficacy and lesser irritation to skin. Hence, the present retinoid-containing topical composition is developed in such a way that it enhances skin deposition of retinoid compound(s) to provide required efficacy and less irritation. These compositions are completely washable immediately after application so that it provides better patient compliance.

Anti-irritants are often interchangeably used with humectants/moisturizers. These excipients tend to have soothing effect on skin dryness caused by foaming agents. The humectant(s) and moisturizers are selected from, but not limited to, urea, glycerin polyhydroxy acids, and ammonium lactate. In certain embodiment disclosed herein, the polyhydroxy acid (PHA) of the topical composition is one of the critical dermatological excipients. These PHAs are alpha hydroxyl acids with multiple hydroxyl groups and act as moisturizers and anti-irritants. The PHA is selected from gluconic acid lactones and aldonic acid lactones such as allonolactone, altronolactone, gluconolactone, mannolactone, gulonolactone, idonolactone, galactonolactone, and talonolactone, PHA is glucono delta-lactone (gluconolactone). Gluconolactone is naturally occurring and used in cosmetic compositions as moisturizer, and humectant. PHA is used in the present composition in the range from about 0.01, 0.1, 1, or 2% w/w to about 3% w/w, from about 0.01% w/w to about 0.1, 1, 2, or 3% w/w, or less than 3% w/w, of total weight of the composition.

U.S. Pat. Nos. 6,036,963 and 5,654,340 disclose glucanolactone as a skin wrinkle treatment agent and an anti-irritant, however these documents do not disclose glucanolactone in the range of about 0.01 to about 3% of the total weight of the composition. Particularly US '963 document discloses at least 3%-8% of glucanolactone as anti-irritant. In the present application, glucanolactone, alone or in combination with tocofersolan, exhibits potent anti-irritant property. Tocofersolan is a polyethylene glycol derivative of α-tocopherol and is water soluble. Tocofersolan is used as Vitamin E supplement and antioxidant in pharmaceutical applications. The percentage weight ratio of glucanolactone to tocofersolan ranges from 0.001:1 to 1:0.001 based on total weight of the composition, or from 0.1:1 to 1:0.1 based on total weight of the composition. In an aspect, the percentage weight ratio of glucanolactone to tocofersolan is 1:2 based on total weight of the composition.

In certain embodiments, foaming agents are important components of retinoid-containing topical compositions, and render cleansing property to topical compositions. These foaming agents can be used alone or in combination thereof. Often, the terms foaming agent and/or surfactant and/or emulsifying agent are used interchangeably and are generally described based on hydrophilic/lipophilic balance (HLB). The HLB scale ranges from 1 (totally lipophilic) to 20 (totally hydrophilic) and is well known in the art; however this scale is not limited by HLB values, for example, sodium lauryl sulfate has a HLB value of 40. In the present application, the term "foaming agent" is commonly used to encompass all of them as described above and interchangeably used with "surfactant".

In some embodiments, the foaming agent(s) used in the present application may be amphiphilic or hydrophilic substances or surfactants. In an aspect, foaming agent(s) used in the present application are selected from, but not limited to, sodium lauryl sulfate, ammonium lauryl sulfate, dioctyl sodium sulfosuccinate, sodium dodecyl benzenesulfonate, sodium dodecyl sulfate, potassium lauryl sulfate; disodium laureth sulfosuccinate, sodium lauroyl sarcosinate, glycerides such as PEG-6 caprylic/capric glycerides, betaines such as cocamidopropyl betaine; ethoxylates such as PEG-10 soya sterol, amides such as cocamide DEA, myristamide DEA, or PEG-20 methyl glucose ether disteartate and ethers, sodium myreth sulfate, sodium stearate, stearyl alcohol, cetyl alcohol, oleyl alcohol, cetostearyl alcohol, poloxamer, polysorbate, sorbitan monostearate, sorbitan tristearate. Other suitable foaming agents additionally or alternatively include, but are not limited to, hydrophilic surfactants such as PEG 400 monooleate, PEG 400 monostearate, potassium oleate, sodium oleate, Polyoxyethylene sorbitan monolaurate (Tween 20), Polyoxyethylene sorbitan monolaurate (Tween 21), Polyoxyethylene sorbitan monopalmitate (Tween 40), Polyoxyethylene sorbitan monostearate (Tween 60), Polyoxyethylene sorbitan monostearate (Tween 61), Polyoxyethylene sorbitan tristearate (Tween 65), Polyoxyethylene sorbitan monooleate (Tween 80), Polyoxyethylene sorbitan monooleate (Tween 81), Polyoxyethylene sorbitan trioleate (Tween 85), cocabetaine, ammonium laureth sulfate and sodium lauryl sulfate or one or more foaming agents selected from detergents, soaps which tend to foam upon contact with water.

The present application relates to a retinoid-containing topical composition comprising a foaming agent in the range from about 0.01, 0.1, 1, 2, 3, 4, 5, 6, 7, 8, or 9% w/w to about 10% w/w, or from about 0.01% w/w to about 0.1, 1, 2, 3, 4, 5, 6, 7, 8, 9, or 10% w/w, based on total weight of the composition or in the range from about 0.1% w/w to about 7% w/w based on total weight of the composition. In certain embodiments disclosed herein, the concentration of foaming agent(s) is one of the critical parts of the invention, because choice and concentration of foaming agent influences the cleansing effect of the topical composition. Certain foaming agents tend to alter the integrity of stratum corneum (SC) thereby exhibiting dryness and irritation to the skin. Moisturizer(s)/emollient(s) balance the effect of foaming agents. For example, in some embodiments, the foaming agent is used from about 0.1% w/w to about 7% w/w based on total weight of the composition, and the foaming agent according to the present application does not cause over dryness to the skin and does not disturb the integrity of stratum corneum.

The hydrophilic surfactants of the present application may be non-ionic, cationic, anionic, amphoteric or zwitterionic. Examples of suitable surfactants include, but not limited to, disodium cocoampho diacetate, oxyethylenated glyceryl cocoate (7 EO), PEG-20 hexadecenyl succinate, PEG-15 stearyl ether, Polyoxyl 20 Cetostearyl Ether, Polypropylene Glycol (PPG)-Stearyl Ether such as PPG-11 Stearyl Ether and PPG-15 Stearyl Ether, Arlamol E, ricinoleic monoethanolamide monosulfosuccinate salts, oxyethylenated hydrogenated ricinoleic triglyceride containing 60 ethylene oxide units such as the products sold by BASF under the trademarks Cremophor® RH 60 or Cremophor® RH 40 (polyoxyl 40 hydrogenated castor oil), polymers such as poloxamers, that are block copolymers of ethylene oxide and propylene oxide, and the nonsolid fatty substances at room temperature (that is to say, at temperatures ranging from about 20 to 35° C.) such as sesame oil, sweet almond oil, apricot stone oil, sunflower oil, octoxyglyceryl palmitate (or 2-ethylhexyl glyceryl ether palmitate), octoxyglyceryl behenate (or 2-ethylhexyl glyceryl ether behenate), dioctyl adipate, and tartrates of branched dialcohols. Sorbitan fatty acid esters are series of mixtures of partial esters of sorbitol and its mono- and dianhydrides with fatty acids. Sorbitan esters include products sold as Arlacel® 20, Arlacel 40, Arlacel 60, Arlacel 80, Arlacel 83, Arlacel 85, Arlacel 987, Arlacel C, PEG-6 stearate and glycol stearate and PEG-32 stearate (Tefose® 63), and PEG-6 stearate and PEG-32 stearate (Tefose® 1500), and any mixtures thereof. Polyethylene glycol ethers of stearic acid are among another group of emulsifiers that can be used in the emulsions. Examples of polyethylene glycol ethers of stearic acid include steareth-2, steareth-4, steareth-6, steareth-7, steareth-10, steareth-11, steareth-13, steareth-15, steareth-20, polyethylene glycol ethers of stearyl alcohol (steareth 21), and any mixtures thereof. Other emulsifying agents include sodium lauryl sulphate, cetyl trialkyl ammonium bromide, polyoxyethylene sorbitan fatty acid esters, and any mixtures thereof.

Nonionic surfactants include those that can be broadly defined as condensation products of long chain alcohols, e.g., C8-30 alcohols, with sugar or starch polymers, i.e., glycosides. Various sugars include, but not limited to, glucose, fructose, mannose, and galactose, and various long chain alcohols include, but not limited to, decyl alcohol, cetyl alcohol, stearyl alcohol, lauryl alcohol, myristyl alcohol, oleyl alcohol, and the like.

Other useful nonionic surfactants include condensation products of alkylene oxides with fatty acids, such as alkylene oxide esters of fatty acids. Other nonionic surfactants are the condensation products of alkylene oxides with 2 moles of fatty acids, such as alkylene oxide diesters of fatty acids.

Examples of amphoteric and zwitterionic surfactants include those that are broadly described as derivatives of aliphatic secondary and tertiary amines in which the aliphatic radical can be straight or branched chain, wherein one of the aliphatic substituents contains from about 8 to about 22 carbon atoms, and one contains an anionic water solubilizing group, e.g., carboxy, sulfonate, sulfate, phosphate, or phosphonate. In an aspect, surfactants include alkylimino acetates, iminodialkanoates and aminoalkanoates, and, imidazolinium and ammonium derivatives. Other suitable amphoteric and zwitterionic surfactants include betaines, sultaines, hydroxysultaines, alkyl sarcosinates, and alkanoyl sarcosinates.

Topical composition of the present application may comprise one or more solvents that include polyols such as glycerol (glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, other glycols, sulfoxides such as dimethylsulfoxide (DMSO), dimethylformanide, methyl dodecyl sulfoxide, dimethylacetamide, monooleate of ethoxylated glycerides (with 8 to 10 ethylene oxide units), azone (1-dodecylazacycloheptan-2-one), 2-(n-nonyl)-1,3-dioxolane, esters such as isopropyl myristate/palmitate, ethyl acetate, butyl acetate, methyl proprionate, capric/caprylic triglycerides, octylmyristate, dodecylmyristate; fatty alcohol/acids or its esters such as olelyl alcohol, cetyl alcohol, myristyl alcohol, stearyl alcohol, lauryl alcohol, lauric acid, lauryl lactate ketones; amides such as acetamide, oleates such as triolein; various alkanoic acids such as caprylic acid; lactam compounds such as azone; alkanols such as ethanol; dialkylamino acetates, and admixtures thereof.

In an aspect, topical composition of the present application comprises retinoid compound(s) in solubilized form, wherein the retinoid compound(s) is solubilized in one or more solvents as mentioned above.

In an aspect, the topical composition of the present application is foamable. Foamability of the composition is known as foaming ability (i.e.) tendency to produce foam of the topical composition required for cleansing dirt or oil substance or sebum in the skin, that provides comfortable foaming sensation during washing, and nice touch during rinsing or after drying, in contrast to detergents for industrial use.

In some embodiments, the topical compositions of the present application are capable of forming a foam by applying manual pressure such as rubbing the composition at application site of the skin or massaging the composition at application site.

In some embodiments, the topical compositions of the present application comprises one or more foaming agents having HLB value which provides foam upon rubbing at application site, for example HLB more than about 10.

The retinoid-containing topical composition of the present application may comprise one or more thickeners selected from, but not limited to, carbomers, polyvinyl pyrrolidone, locust gum, polyvinyl alcohol, cross-linked polyacrylate polymer, guar gum, locust bean gum, polysaccharides, and cellulose polymers such as carboxymethyl cellulose, methocel (HPMC), hydroxyethyl cellulose, hydroxypropylcellulose, and mixtures thereof.

The retinoid-containing topical composition of the present application may comprise one or more pH adjusting agents, selected from, but not limited to, calcium hydroxide, sodium hydroxide, potassium hydroxide, and amines such as triethanolamine. In an embodiment, triethanolamine (also known as trolamine) is a pH-adjusting agent.

The term "emollients" are used to denote the substances that soften and soothe the skin. They are used to correct dryness and scaling of the skin. Retinoid-containing topical composition of the present application may comprise one or more emollients selected from, but not limited to, oils of natural origin such as almond oil, coconut oil, olive oil, palm oil, peanut oil and the like, fatty acids such as lauric acid, myristic acid, palmitic acid, and stearic acid, monohydric alcohol esters of the fatty acids such as ethyl laurate, isopropyl laurate, ethyl myristate, n-propyl myristate, isopropyl myristate, ethyl palmitate, isopropyl palmitate, methyl palmitate, methyl stearate, ethyl stearate, isopropyl stearate, butyl stearate, isobutyl stearate, amyl stearate, and isoamyl stearate, glycols such as ethylene glycol, diethylene glycol, polyethylene glycol, and propylene glycol, branched aliphatic alcohols such as lauryl alcohol, myristyl alcohol, and stearyl alcohol, and mixture of fatty alcohols comprising cetyl and stearyl alcohols such as cetearyl alcohol, mineral oil, and any combinations thereof.

The term "antioxidants" is used to denote the substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. The retinoid-containing topical composition of the present application may comprise one or more antioxdants, selected from, but not limited to, ascorbic acid (vitamin C), glutathione, lipoic acid, uric acid, carotenes, α-tocopherol (vitamin E), tocofersolan, ubiquinol, butylated hydroxyanisole, butylated hydroxytoluene, sodium benzoate, propyl gallate (PG, E310), and tertiary-butylhydroquinone. The amounts of antioxidants may be from about 0.01% to about 10%, of the total weight of the composition.

The term "preservative" refers to a natural or a synthetic chemical that is added to products to prevent decomposition by microbial growth or by undesirable chemical changes. Preservatives can desirably be incorporated into a composition for the protection against the growth of potentially harmful microorganisms. While microorganisms tend to grow in an aqueous phase, these can also reside in a hydrophobic or an oil phase. The retinoid-containing topical composition of the present application may comprise one or more preservatives, selected from, but not limited to, methylparaben, propylparaben, benzyl alcohol, chlorocresol, benzalkonium chloride, cetrimonium chloride, sodium edetate, boric acid, sorbic acid, potassium sorbate, sodium benzoate, methylchloro isothiazolinone, methyl isothiazolinone, diazolidinyl urea, Imidazolidinyl urea, and any mixtures thereof. The amount of preservative may be from about 0.25% to about 2.5, 5, 10, 15, 20 or 25% w/w of the total weight of the composition.

In an aspect, retinoid-containing topical composition optionally comprises a chelating agent. The chelating agents are selected from, but not limited to, ethylenediamine tetraacetic acid (EDTA), diammonium EDTA, dipotassium EDTA, calcium disodium EDTA, H-EDTA, TEA-EDTA, tetrasodium EDTA, tripotassium EDTA, trisodium phosphate, diammonium citrate, galactaric acid, galacturonic acid, gluconic acid, glucuronic acid, humic acid, cyclodextrin, potassium citrate, the potassium salt of ethylenediamine-tetra (methylene phosphonic acid) (EDTMP), sodium citrate, sodium EDTMP, and the like, and any mixtures thereof.

Another aspect of the present application relates to an aqueous-based retinoid containing topical composition comprising: a) tazarotene; b) at least one foaming agent; c) at least one anti-irritant; and d) one or more dermatologically acceptable excipients, wherein the topical composition contains at least about 60% w/w of water based on the total weight of the composition.

Another aspect of the present application relates to a retinoid containing topical composition comprising: a) tazarotene; b) at least one foaming agent; c) at least one anti-irritant; and d) one or more dermatologically acceptable excipients, wherein said at least one anti-irritant is polyhydroxy acid or tocofersolan.

Another aspect of the present application relates to a retinoid containing topical composition comprising: a) tazarotene; b) at least one foaming agent; c) at least one anti-irritant; and d) one or more dermatologically acceptable excipients, wherein said at least one anti-irritant is gluconolactone and tocofersolan.

In an aspect, the present application relates to an aqueous-based retinoid-containing topical composition comprising: a) from about 0.01% w/w to about 1% w/w of tazarotene or pharmaceutically acceptable salts or esters thereof; b) from about 0.1% w/w to about 7% w/w of foaming agents selected from disodium laureth sulfosuccinate, cocobetaine, sodium lauryl sarcosinate, and sodium lauryl sulfate, or mixtures thereof; c) from about 0.01% w/w to about 3% w/w of a polyhydroxy acid as an anti-irritant; and d) one or more dermatologically acceptable excipients selected from emollients, antioxidants, solubilizers, viscosity modifiers, stabilizers, pH adjusting agents, preservatives, fatty alcohols, fatty acid esters and polymers, and moisturizers, wherein said composition comprises at least about 60% w/w water based on the final weight of the composition.

In an aspect, retinoid-containing topical composition of the present application provides an effective amount of tazarotene to the skin layer, wherein said topical composition provides 0.01 μg to 10 μg of tazarotene concentration in the skin layer that comprises epidermis and/or dermis. The retinoid-containing topical composition of the present application provides more concentration of tazarotene in the epidermis layer than the dermis layer.

In certain embodiments, the topical composition of the present application comprises tazarotene that is deposited in the affected area of the skin at a concentration of more than 0.1% of TAZORAC topical gel.

In some embodiments, the topical composition of present application comprises tazarotene and/or pharmaceutically acceptable salts thereof, wherein tazarotene is suspended in the composition. In an aspect of the present application, tazarotene is in micronized form. In another aspect, the particle size of micronized tazarotene has D90 less than about 70 μm, or D90 is in the range from about 5 μm to about 60 μm, or D90 is about 10 μm. In a further aspect, the particle size of micronized tazarotene has D50 less than about 500 μm, or D50 is in the range from about 50 μm to about 100 μm, or D50 is about 10 μm.

In an aspect, the topical composition of the present application comprises tazarotene and/or pharmaceutically acceptable salts thereof, wherein tazarotene is in the suspended form. In a specific aspect, said composition is pH balanced and stable. In another aspect, tazarotene tends to dissolve at a pH below 3 which causes degradation.

In an aspect, the present application relates to a stable retinoid-containing topical composition. The term "stable" as used herein refers to physical stability and/or chemical stability of the active agent in the composition, wherein changes in the drug assay values and/or impurities content are less than about 5%, during storage stability study of the composition at 25° C. and 60% relative humidity (RH), or 30° C. and 65% RH, or 40° C. and 75% RH, for durations such as 3, 6, 12, 18, or 24 months.

In an aspect, the topical composition comprises tazarotene and optionally contains one or more of related substances, such as impurity A (methyl 6-[(4,4-dimethyl-3,4-dihydro-2H thiochromen-6-yl) ethynyl] nicotinate) in amounts not more than about 0.1%; impurity B (ethyl 6-[(4,4-dimethyl-1-oxido-3,4-dihydro-2H-thiochromen-6-yl) ethynyl] nicotinate) in amounts not more than about 2%; impurity C (6-[(4,4-dimethyl-3,4-dihydro-2H-thiochromen-6-yl)ethynyl] nicotinic acid) in amounts not more than about 0.1%. The above impurity limits are expressed as percentages of the label drug content in the topical composition.

In an aspect, the present application relates to a method of treating skin disorders by retinoid-containing topical composition comprising: a) shaking the composition; b) topically applying the composition to the affected area of the skin for a period of about 0 seconds to about 15 minute; and c) rinsing-off said composition from the affected area with water or suitable solvent. In an aspect, said minimum period of time is from about 30 seconds to about 10 minutes. In an aspect, said minimum period of time is from about 30 seconds to about 5 minutes.

In an aspect, the present application relates to a method of treating acne in a patient in need thereof, comprising topically administering retinoid-containing topical composition of the present application, wherein said composition administers an effective amount of retinoid compound(s) to the skin.

In an aspect, the present application relates to a method of treating acne vulgaris in a patient in need thereof, comprising topically administering the topical composition comprising: a) from about 0.01% w/w to about 1% w/w of tazarotene or pharmaceutically acceptable salts, esters thereof; b) from about 0.1% w/w to about 7% w/w of foaming agents selected from disodium laureth sulfosuccinate, cocobetaine, sodium lauryl sarcosinate, and sodium lauryl sulfate, or mixtures thereof; c) from about 0.01% w/w to about 3% w/w of an anti-irritant selected from polyhydroxy acids; and d) one or more dermatologically acceptable excipients selected from emollients, antioxidants, solubilizers, viscosity modifiers, stabilizers, pH adjusting agents, preservatives, fatty alcohols, fatty acid esters and polymers, and moisturizers.

Another aspect of the present application relates to a process of preparing retinoid-containing topical composition comprising the steps of: 1) preparing retinoid-containing dispersion comprising: mixing retinoid compound with foaming agent and water; 2) preparing an emulsion by mixing aqueous phase and oil phase under homogenization; 3) preparing the composition by mixing retinoid-containing dispersion and emulsion together under homogenization; 4) and adjusting the pH of the retinoid-containing topical composition using a suitable pH adjusting agent in the range of about 4 to about 7.

An aspect of the present application further provides a process for preparing retinoid-containing topical composition to be filled into any suitable dispensing device. In an aspect, a process of preparing retinoid-containing topical composition comprises the steps of: 1) preparing aqueous phase comprising: mixing: a) sufficient quantity of water, b) humectant and/or moisturizer, c) preservative(s) d) foaming agent, and other suitable excipients, at a desired temperature under homogenization, wherein due care is taken to avoid foam during homogenization; 2) preparing oil phase comprising: mixing solvent optionally with emollients, lipid soluble antioxidants etc. at a desired temperature under homogenization; 3) preparing emulsion comprising: mixing aqueous phase of step 1 and oil phase of step 2 at a desired temperature under homogenization, and optionally adjusting the pH to a desired level; 4) preparing drug-containing dispersion comprising: mixing a) retinoid, b) foaming agent, and c) water at a desired temperature under homogenization; and 5) preparing the composition by mixing drug dispersion of step 4 and emulsion of step 3 at a desired temperature under homogenization, and adjusting the pH to a desired level.

In one aspect, the topical compositions of the present application comprises at least one oil phase and one hydrophilic phase. For example, in some embodiments, the topical composition of present application is a biphasic composition such as oil-in-water emulsion, or water-in-oil emulsion, or suspension, or suspension gel or monophasic composition such as suspension, or suspension gel.

In an aspect, the oil phase of the topical composition of the present application comprises one or more water immiscible substances that can act as emollient. Suitable water immiscible substances that can be used in the present application are selected from, but not limited to, vegetable oils, derivatives of vegetable oils, medium chain triglycerides (naturally occurring/isolated from natural source or synthetic), vitamin E or its derivatives, water immiscible emollient substances, fatty alcohols and the like or mixtures thereof. The fatty alcohols are selected from, but not limited to, lauryl alcohol, stearyl alcohol, cetostearyl alcohol, cetyl alcohol, oleyl alcohol or mixtures thereof. The vegetable oils are selected from, but limited to, soybean oil, corn oil, safflower oil, sesame oil, olive oil, castor oil or a mixture thereof. The medium chain triglycerides are medium chain fatty acids esterified with glycerides, which are selected from, but not limited to, capric/caprylic triglycerides.

In another aspect, the oil phase of the present topical composition is interchangeably referred to as emollients. In another aspect, the topical composition of the present application without the active substance is interchangeably referred to as emollient base composition or emollient vehicle.

In an aspect, the oil phase present in the composition of present application in an amount of about 0% to about 40% based on the total weight of the composition, or from about 1% to about 30% based on the total weight of the composition or from about 1% to about 20% based on the total weight of the composition.

In an aspect, the hydrophilic phase of the topical compositions of the present application comprises one or more excipients selected from water, gelling agent, foaming agent, pH adjusting agent, humectant, preservatives, antioxidants, anti-irritants, and the like.

In another aspect, the hydrophilic phase present in the composition of present application comprises at least about 60% of water or at least about 70% of water or at least about 80% of water.

The concentration of gelling agent is critical in terms of flow properties of the composition. Higher concentration of gelling agent indicates high viscosity and short flow properties of the composition. In an aspect, the gelling agent used in the present application is present in the amount of from about 0.01% to about 2%. In another aspect, the gelling agent is present in an amount of from about 0.1% to about 1%.

In another aspect, the topical composition of present application is capable of forming foam.

In another aspect, the topical composition of present application is non-sprayable.

In another aspect, the topical composition of present application is non-sprayable and pourable liquid topical dosage form, wherein said composition is in the form of suspension, emulsion or lotion.

In another aspect, the topical composition of present application is propellant free.

In another aspect, the topical composition of present application is homogenous suspension or suspension gel or emulgel.

In another aspect, the topical composition of present application comprises substantial amount of tazarotene or its pharmaceutically acceptable salts or esters thereof, in the hydrophilic phase. The term "substantial amount" as used herein denotes at least about 80% of label amount of the active substance or at least about 90% of label amount of the active substance or at least about 95% of label amount of the active substance or at least about 100% of label amount of the active substance. The term "substantial amount in hydrophilic phase" as denoted in the context of the present application comprises at least about 80% of label amount of the active substance suspended in hydrophilic phase of the topical composition.

In another aspect, the topical composition of present application is storage stable. The term "storage stable" as used herein denotes physical stability of the topical composition at controlled room temperature without phase separation or particle ripening i.e. suspended particle aggregation, or sedimentation or precipitation or change in color or any such physical attributes.

In another aspect of the present application, the tazarotene used in the topical composition of the present application has D90 particle size of not more than about 50 microns, or not more than about 40 microns, or not more than about 30 microns, or not more than about 20 microns.

In another aspect, the oil phase used in the composition of the present application has D90 globule size of not more than about 50 microns, or not more than about 40 microns, or not more than about 30 microns, or not more than about 20 microns, or not more than about 10 microns.

In another aspect, the topical composition of the present application is storage stable and does not show any variations in the oil globule size at least for 3 months at 25° C. or at least for 6 months at 25° C. or at least for 9 months at 25° C. or at least for 12 months at 25° C. or at least for 24 months at 25° C.

In another aspect, the topical composition of the present application is storage stable and does not show any phase separation at least for 3 months at 25° C. or at least for 6 months at 25° C. or at least for 9 months at 25° C. or at least for 12 months at 25° C.

In an aspect, the present application relates to a topical composition comprising: a) tazarotene or its pharmaceutically acceptable salts or esters thereof; b) at least one foaming agent; c) an anti-irritant selected from polyhydroxy acids; and d) one or more dermatologically acceptable excipients wherein said composition is homogenous suspension containing tazarotene in suspended form.

In an aspect, the present application relates to a topical composition comprising: a) tazarotene; b) at least one foaming agent; c) at least one anti-irritant; and d) one or more dermatologically acceptable excipients, wherein said anti-irritant is selected from polyhydroxy acids in the range of about 0.01% to about 3% of the total weight of the composition, and said composition is storage stable.

In an aspect, the present application relates to a topical composition comprising: a) tazarotene; b) at least one foaming agent; c) at least one anti-irritant; and d) one or more dermatologically acceptable excipients, wherein said anti-irritant is selected from polyhydroxy acids in the range of about 0.01% to about 3% of the total weight of the composition, and said composition is storage stable having D90 globule size of oil phase not more than about 50 microns.

In an aspect, the present application relates to a topical composition comprising: a) tazarotene; b) at least one foaming agent; c) at least one anti-irritant; and d) one or more dermatologically acceptable excipients, wherein said anti-irritant is selected from polyhydroxy acids in the range of about 0.01% to about 3% of the total weight of the composition, and said composition is storage stable having D90 globule size of oil phase not more than about 50 microns and D90 particle size of said tazarotene not more than about 50 microns.

In an aspect, the present application relates to a topical composition comprising: a) tazarotene; b) at least one foaming agent; c) at least one anti-irritant; and d) one or more dermatologically acceptable excipients, wherein said anti-irritant is selected from polyhydroxy acids in the range of about 0.01% to about 3% of the total weight of the composition, and said composition is storage stable and pH of said composition is from about 4 to about 7.

In an aspect, the present application relates to a topical composition comprising: a) tazarotene; b) at least one foaming agent; c) at least one anti-irritant; and d) one or more dermatologically acceptable excipients, wherein said anti-irritant is selected from polyhydroxy acids in the range of about 0.01% to about 3% of the total weight of the composition, and said composition is storage stable and pH of said composition is from about 4 to about 7; wherein said tazarotene is suspended in the composition.

In another aspect, the oil phase has D90 globule size of not more than about 50 microns or not more than about 40 microns, or not more than about 30 microns, or not more than about 20 microns, or not more than about 10 microns. In some aspects, the oil phase has D50 globule size of not more than about 30 microns, or not more than about 20 microns, or not more than about 10 microns or not more than about 5 microns. In some aspects, the oil phase has D10 globule size of not more than about 10 microns, or not more than about 5 microns. In yet another aspect, the topical compositions of the present application are interchangeably referred to as microemulsion or emulgel or suspension gel or foamable suspension gel or foaming gel.

In an aspect, the present application relates to a topical composition comprising: a) tazarotene or its pharmaceutically acceptable salts or esters thereof; b) one or more foaming agents having HLB value of more than about 10; c) an anti-irritant selected from polyhydroxy acids; and d) one or more dermatologically acceptable excipients; wherein said composition tends to form foam upon rubbing at application site of the subject skin.

In an aspect, the composition is of the present application is foamable at the application site, upon applying manual act such as rubbing or massaging, and the foaming tendency of the composition increases while applying to the wet skin.

In an aspect, the present application relates to a topical composition comprising: a) tazarotene or its pharmaceutically acceptable salts or esters thereof; b) one or more foaming agents having HLB value of more than about 10; and c) one or more dermatologically acceptable excipients; wherein said composition tends to form foam upon rubbing at application site of the subject skin.

In an aspect, the present application relates to a topical composition comprising: a) tazarotene or its pharmaceutically acceptable salts or esters thereof; b) one or more foaming agents having HLB value of more than about 10; and c) one or more dermatologically acceptable excipients; wherein said tazarotene is present in suspended form and the D90 particle size of the tazarotene is not more than about 50 microns or not more than about 40 microns, or not more than about 30 microns, or not more than about 20 microns.

In an aspect, the present application relates to a topical composition comprising: a) tazarotene or its pharmaceutically acceptable salts or esters thereof; b) one or more foaming agents having HLB value of more than about 10; c) an anti-irritant selected from polyhydroxy acids; and d) one or more dermatologically acceptable excipients; wherein said tazarotene is present in suspended form and the D90 particle size of the tazarotene is not more than about 50 microns or not more than about 40 microns, or not more than about 30 microns, or not more than about 20 microns.

In an aspect, the present application relates to a topical composition comprising: a) tazarotene or its pharmaceutically acceptable salts or esters thereof; b) one or more foaming agents having HLB value of more than about 10; c) an anti-irritant selected from polyhydroxy acids; and d) one or more dermatologically acceptable excipients; wherein said tazarotene is present in suspended form and the D90 particle size of the tazarotene is not more than about 50 microns.

In an aspect, the present application relates to a topical composition comprising: a) tazarotene or its pharmaceutically acceptable salts or esters thereof; b) one or more foaming agents having HLB value of more than about 10; c) an anti-irritant selected from polyhydroxy acids; and d) one or more dermatologically acceptable excipients; wherein said tazarotene is present in suspended form and the D90 particle size of the tazarotene is not more than about 40 microns.

In an aspect, the present application relates to a topical composition comprising: a) tazarotene or its pharmaceutically acceptable salts or esters thereof; b) one or more foaming agents having HLB value of more than about 10; c) an anti-irritant selected from polyhydroxy acids; and d) one or more dermatologically acceptable excipients; wherein said tazarotene is present in suspended form and the D90 particle size of the tazarotene is not more than about 30 microns. C.

In an aspect, the present application relates to a topical composition comprising: a) tazarotene; b) one or more foaming agent; c) an oil phase comprising one or more water immiscible substances; d) a hydrophilic phase comprising water; and e) one or more dermatologically acceptable excipient.

In an aspect, the present application relates to a topical composition comprising: a) tazarotene; b) one or more foaming agents; c) an oil phase comprising one or more water immiscible substances; d) a hydrophilic phase comprising water; and e) one or more dermatologically acceptable excipients; wherein said composition further comprises an anti-irritant selected from polyhydroxy acid in the range of about 0.1% w/w to about 3% w/w based on total weight of the composition.

In an aspect, the present application relates to a topical composition comprising: a) tazarotene; b) one or more foaming agents; c) an oil phase comprising one or more water immiscible substances; d) a hydrophilic phase comprising water; and e) one or more dermatologically acceptable excipient; wherein said composition is storage stable.

In an aspect, the present application relates to a topical composition comprising: a) tazarotene; b) one or more foaming agents; c) an oil phase comprising one or more water immiscible substances; d) a hydrophilic phase comprising water; and e) one or more dermatologically acceptable excipient; wherein said composition is storage stable and D90 particle size of tazarotene is less than about 50 microns.

In an aspect, the present application relates to a topical composition comprising: a) tazarotene; b) one or more foaming agents; c) an oil phase comprising one or more water immiscible substances; d) a hydrophilic phase comprising water; and e) one or more dermatologically acceptable excipient; wherein said composition is storage stable and D90 globule size of oil phase is less than about 50 microns.

In an aspect, the present application relates to a topical composition comprising: a) tazarotene; b) one or more foaming agents; c) an oil phase comprising one or more water immiscible substances; d) a hydrophilic phase comprising water; and e) one or more dermatologically acceptable excipient; wherein said composition is storage stable and D90 particle size of tazarotene is less than about 50 microns and D90 globule size of oil phase is less than about 50 microns, and said composition does not show change in particle size and/or globule size at least for about 3 months at 25° C. or at least for about 6 months at 25° C. or at least for about 9 months at 25° C. or at least for about 12 months at 25° C. or at least for about 24 months at 25° C.

In an aspect, the present application relates to a topical composition comprising: a) tazarotene; b) one or more foaming agents; c) an oil phase comprising one or more water immiscible substances; d) a hydrophilic phase comprising water; and e) one or more dermatologically acceptable excipients; wherein substantial amount of said tazarotene is present in a hydrophilic phase and the D90 particle size of the tazarotene is not more than about 50 microns or not more than about 40 microns, or not more than about 30 microns, or not more than about 20 microns.

In an aspect, the present application relates to a topical composition comprising: a) tazarotene or its pharmaceutically acceptable salts or esters thereof; b) one or more foaming agents having HLB value more than about 10; c) an anti-irritant selected from polyhydroxy acids; d) an oil phase comprising one or more water immiscible substances; e) a hydrophilic phase comprising water; and f) one or more dermatologically acceptable excipients; wherein substantial amount of said tazarotene is present in the hydrophilic phase and the D90 particle size of the tazarotene is not more than about 50 microns or not more than about 40 microns, or not more than about 30 microns, or not more than about 20 microns.

In an aspect, the present application relates to a topical composition comprising: a) tazarotene or its pharmaceutically acceptable salts or esters thereof; b) one or more foaming agents; c) a gelling agent; d) an oil phase; e) a hydrophilic phase comprising water; and f) one or more dermatologically acceptable excipients; wherein said composition is a suspension in which tazarotene is suspended by gelling agent, and the D90 particle size of the tazarotene is not more than about 50 microns or not more than about 40 microns, or not more than about 30 microns, or not more than about 20 microns.

In an aspect, the present application relates to a topical composition comprising: a) tazarotene or its pharmaceutically acceptable salts or esters thereof; b) one or more foaming agents; c) a gelling agent; d) an oil phase comprising one or more water immiscible substances; e) a hydrophilic phase comprising water; f) an anti-irritant selected from polyhydroxy acids; and g) one or more dermatologically acceptable excipients; wherein said composition is a suspension in which tazarotene is suspended by gelling agent, and the D90 particle size of the tazarotene is not more than about 50 microns or not more than about 40 microns, or not more than about 30 microns, or not more than about 20 microns.

In an aspect, the present application relates to a topical composition comprising: a) tazarotene or its pharmaceutically acceptable salts or esters thereof; b) one or more foaming agents having HLB value more than about 10; c) an oil phase comprising one or more fatty alcohols; c) a hydrophilic phase comprising substantial amount of tazarotene, an anti-irritant selected from polyhydroxy acid in the range of about 0.01% to about 3% of the total weight of the composition, water not less than 50%; wherein said composition is foamable and propellant free.

In an aspect, the present application relates to a topical composition comprising: a) tazarotene or its pharmaceutically acceptable salts or esters thereof; b) one or more foaming agents having HLB value more than about 10; c) an oil phase comprising one or more fatty alcohols; c) a hydrophilic phase comprising substantial amount of tazarotene, an anti-irritant selected from polyhydroxy acid in the range of about 0.01% to about 3% of the total weight of the composition, water not less than 50%; wherein said composition is capable of forming foaming, upon applying at application site.

As described above, in some embodiments, the topical composition of the present application is foamable. In one aspect, the foaming capacity of compositions of the present application is from about 5 ml to about 120 ml.

In an aspect, the foaming capacity of the compositions of the present application is from about 10 ml to about 100 ml, or from about 15 ml to about 95 ml, or from about 20 ml to about 90 ml. In some other aspects, the foaming capacity of the topical compositions of the present application is not less than about 10 ml, and not more than about 50 ml.

In some embodiments, tazarotene undergoes degradation in the presence of excipients which causes oxidation, for example alpha hydroxyl acid, polysorbate, benzyl alcohol, isostearic acid and the like.

In an aspect, the topical composition of the present application is free of alpha or beta hydroxy acids such as lactic acid, or glycolic acid.

In an aspect, the topical composition of the present application is free of lactic acid.

In an aspect, the topical composition of the present application is free of glycolic acid.

In an aspect, the topical composition of the present application is free of benzyl alcohol.

In one aspect, the present application relates to a topical composition comprising tazarotene, wherein said tazarotene is not in a solubilized form, but in suspended form. Yet the content uniformity of tazarotene in the dosage form is maintained.

In an aspect, the topical composition of the present application comprises: a) tazarotene or its pharmaceutically acceptable salts or esters thereof; b) one or more anti-irritants selected from polyhydroxy acid, Vitamin E derivative or mixtures thereof, in an amount of about 0.1% to about 3%; c) one or more foaming agents selected from sodium lauryl sulphate, disodium laureth sulfosuccinate, cocobetaine, sodium lauroyl sarcosinate or mixtures thereof, in an amount of about 0.1% to about 10%; and d) one or more pharmaceutically acceptable excipients; wherein said tazarotene is suspended in the composition and said composition is in the form of monophasic gel.

In another aspect, the topical composition of the present application is in the form of oil-in-water emulsion, comprising: a) hydrophilic phase comprising i) tazarotene or its pharmaceutically acceptable salts or esters thereof and ii) a gelling agent; b) an oil phase comprising one or more water immiscible substances, selected from fatty alcohols, vegetable oils, medium chain triglycerides mineral oil or mixtures thereof; c) one or more foaming agents selected from sodium lauryl sulphate, disodium laureth sulfosuccinate, cocobetaine, or sodium lauroyl sarcosinate or mixtures thereof, in an amount of about 0.1% to about 10%; and d) one or more pharmaceutically acceptable excipients; wherein said tazarotene is suspended in the hydrophilic phase and said composition has a pH of about 4 to about 7.

In an aspect, the topical composition of the present application is prepared by a process comprising a pre-neutralization step.

In another aspect, the present invention relates to a process of preparing topical composition comprising tazarotene or its pharmaceutically acceptable salts or esters thereof, wherein said process comprises steps of: a) preparing an oil phase, b) preparing a hydrophilic phase, c) preparing the tazarotene phase, and d) emulsification, wherein said tazarotene phase is added after emulsification, and said emulsification step further comprises pre-neutralization step using pH adjusting agent to pH of above about 5.

The pre-neutralization step is carried out by the addition of a pH adjusting agent such as sodium hydroxide, triethanolamine, citric acid, hydrochloric acid and the like. The pre-neutralization step is carried out to prevent the solubilization of tazarotene in the oil phase comprising one or more medium chain triglycerides. In the lower pH tazarotene tend to solubilize in oil phase, leading to tazarotene degradation in the solubilized form.

In another aspect, the topical composition of the present application is in the form of oil-in-water emulsion, and comprises: a) hydrophilic phase comprising i) tazarotene or its pharmaceutically acceptable salts or esters thereof, from about 0.01% to about 0.2%, ii) a gelling agent, and iii) water; b) an oil phase; c) one or more foaming agent; and d) one or more pharmaceutically acceptable excipients; wherein said tazarotene is suspended in hydrophilic phase, and said composition is prepared by a process comprising pre-neutralization step to prevent solubilization of tazarotene.

In an aspect, the present application relates to a process of preparing topical composition comprising tazarotene or its pharmaceutically acceptable salts or esters thereof, wherein the process comprises steps of: a) preparing a hydrophilic phase comprising water and a gelling agent; b) preparing an oil phase comprising one or more emollient substances; c) emulsification and pre-neutralization to adjust the pH from about 4 to about 7; d) preparing tazarotene phase comprising tazarotene and water; and e) homogenizing the tazarotene phase with emulsion of step c.

In one aspect, the pharmacokinetic parameters of compositions of the present application are compared with TAZORAC® cream.

As used herein, the term "TAZORAC®" refers to any topical composition comprising tazarotene in the strength of 0.1%, which are pharmaceutical equivalent, therapeutically equivalent, bioequivalent as defined by US FDA, and said topical composition can be in any suitable topical dosage form. TAZORAC® is a registered trademark of Allergan Inc. and is available as cream and gel. For example, TAZORAC® cream contains tazarotene 0.1% and the following inactive ingredients: benzyl alcohol 1%, carbomer 1342, carbomer homopolymer type B, edetate disodium, medium chain triglycerides, mineral oil, purified water, sodium hydroxide, sodium thiosulfate, and TAZORAC® gel contains tazarotene 0.1% and the following inactive ingredients: sorbitan monooleate and ascorbic acid, butylated hydroxyanisole, butylated hydroxytoluene, carbomer homopolymer type B, edetate disodium, hexylene glycol, poloxamer 407, polyethylene glycol 400, polysorbate 40, purified water and tromethamine.

In one aspect, "tazarotene" is administered as pharmaceutically acceptable form, including, but not limited to, tazarotene or its pharmaceutically acceptable salts, esters, isomers, prodrugs or mixtures thereof. Upon administration tazarotene provides tazarotenic acid, its active metabolite in the system.

In an aspect, the present application relates to a topical composition comprising tazarotene, wherein said composition provides systemic exposure of tazarotene and/or tazarotenic acid, less than or similar as compared to TAZORAC® cream.

The term "systemic exposure" as used herein denotes an amount of tazarotene and/or its active metabolite (tazarotenic acid) available in the systemic circulation of the subject, pre or post topical application of composition of the present application and said systemic exposure of tazarotene and/or tazarotenic acid is defined in terms of pharmacokinetic parameters such as Area under curve ($AUC_{0-12}$, or $AUC_{0-24}$), or maximum plasma concentration ($C_{max}$) or time to reach maximum concentration ($T_{max}$). The subjects for pharmacokinetic study are selected from healthy human volunteers, or subject with skin disorders such as psoriasis or acne vulgaris, or a mammalian animal such as rat, mice and the like. Said pharmacokinetic parameters are expressed as mean values obtained from subjects using various statistical methods known, such as natural logarithmic transformation etc. and the values mentioned herein are statistically significant $p<0.001$ or $p<0.05$ or 90% co-efficient of variation or 90% confidence interval or 95% confidence interval or 99% confidence interval.

In an aspect, the present application relates to a topical composition comprising: a) tazarotene; b) an anti-irritant; c) a foaming agent; and d) a pharmaceutically acceptable excipient; wherein said composition provides systemic exposure of tazarotene and/or tazarotenic acid, less than or similar as compared to TAZORAC®.

In an aspect, the present application relates to a topical composition comprising: a) tazarotene; b) an anti-irritant; c) a foaming agent; and d) a pharmaceutically acceptable excipient; wherein said composition provides systemic exposure of tazarotene and/or tazarotenic acid, less than or similar as compared to TAZORAC® cream.

In an aspect, the present application relates to a topical composition comprising: a) tazarotene; b) an anti-irritant selected from polyhydroxy acids; c) a foaming agent selected from disodium laureth sulfosuccinate, cocobetaine, sodium lauryl sarcosinate, and sodium lauryl sulfate; and d) a pharmaceutically acceptable excipient; wherein said composition provides systemic exposure of tazarotene and/or tazarotenic acid, less than or similar as compared to TAZORAC®.

In another aspect, TAZORAC® is TAZORAC® cream.
In another aspect, TAZORAC® is TAZORAC® gel.
In an aspect, the present application relates to a method of administering topical composition comprising tazarotene to a subject once or twice daily.

The topical treatment with TAZORAC® involves application of the product to a subject's affected area as a thin film (2 mg/cm2) once per day, especially in the evening time, for the treatment of psoriasis or acne vulgaris. The topical compositions of the present application are applied to the affected area of the subject and rinsed off immediately or within 5 minutes provides similar or less systemic exposure of tazarotene and/or tazarotenic acid as compared to TAZORAC® cream applied overnight.

The administration of topical composition of the present application involves administration of the composition and rinsed off within 5 minutes from administration, yet the systemic exposure of tazarotene and/or tazarotenic acid is similar or less than the TAZORAC® cream once daily overnight application (12 hours).

The topical composition of the present application comprising tazarotene, is intended for administering as washable composition to a subject and said administration is not left over for a time period but is rinsed off immediately i.e. within 5 minutes.

The topical composition of the present application provides less systemic exposure of tazarotene and/or tazarotenic acid in the subject's plasma. The minimum contact time application of topical composition of present application provides tazarotene deposition at skin layer which provides retinoid activity to elicit therapeutic effect in the affected area.

In an aspect, the present application relates to a method of administering a topical composition of tazarotene to a subject; wherein said method comprises: spreading, gentle rubbing or massaging; and allowing the composition to remain in the affected area for a minimum period of time, wherein said minimum period of time is less than about 5 minutes; wherein said method provides systemic exposure of tazarotene and/or tazarotenic acid, less than or similar as compared to TAZORAC®, for example as compared to TAZORAC® cream.

In another aspect, the minimum period of time is less than about 4 minutes, or less than about 3 minutes or less than about 2 minutes or less than about 1 minute.

In an aspect, the topical composition is a topical wash composition i.e. easily washable composition, and rinsed off within 5 minutes from application site, and provides therapeutically effective concentration to the skin, and systemic exposure of tazarotene and/or tazarotenic acid is less or similar as compared to TAZORAC® cream. Said topical composition is administered once or twice daily with minimum contact time of less than about 5 minutes.

In an aspect, the topical composition of present application provides less systemic exposure of tazarotene and/or tazarotenic acid, when administered once daily for 14 days as compared to TAZORAC® cream.

In an aspect, the topical composition of present application provides similar systemic exposure of tazarotene and/or tazarotenic acid, when administered twice daily for 14 days as compared to TAZORAC® cream.

The term "about" in the context of pharmacokinetic parameters is modifying term from the absolute value mentioned over there. The term "about" in the context of $AUC_{0-24}$ is ±100 pg·h/ml or is ±90 pg·h/ml or is ±80 pg·h/ml or is ±70 pg·h/ml or is ±60 pg·h/ml or is ±50 pg·h/ml or is ±40 pg·h/ml or is ±30 pg·h/ml or is ±20 pg·h/ml or is ±10 pg·h/ml. The term "about" in the context of $C_{max}$ is ±100 pg/ml or is ±90 pg/ml or is ±80 pg/ml or is ±70 pg/ml or is ±60 pg/ml or is ±50 pg/ml or is ±40 pg/ml or is ±30 pg/ml or is ±20 pg/ml or is ±10 pg/ml.

In an aspect, the topical composition of the present application comprising tazarotene provides systemic exposure (mean $AUC_{0-24}$) of tazarotenic acid less than about 2550 pg·h/ml on day 1 post treatment, when administered as topical composition twice daily for 14 days.

In an aspect, the topical composition of the present application comprising tazarotene provides systemic exposure (mean $AUC_{0-24}$) of tazarotenic acid about 1690 pg·h/ml on day 1 post treatment, when administered as topical composition twice daily for 14 days.

In an aspect, the topical composition of the present application comprising tazarotene provides systemic exposure (mean $AUC_{0-24}$) of tazarotenic acid less than about 3875 pg·h/ml on day 7, when administered as topical composition twice daily for 14 days.

In an aspect, the topical composition of the present application comprising tazarotene provides systemic exposure (mean AUC$_{0-24}$) of tazarotenic acid about 3515 pg·h/ml on day 7, when administered as topical composition twice daily for 14 days.

In an aspect, the topical composition of the present application comprising tazarotene provides systemic exposure (mean AUC$_{0-24}$) of tazarotenic acid less than about 5410 pg·h/ml on day 14, when administered as topical composition twice daily for 14 days.

In an aspect, the topical composition of the present application comprising tazarotene provides systemic exposure (mean AUC$_{0-24}$) of tazarotenic acid about 4310 pg·h/ml on day 14, when administered as topical composition twice daily for 14 days.

In an aspect, the topical composition of the present application comprising tazarotene provides systemic exposure (mean AUC$_{0-24}$) of tazarotenic acid less than about 1200 pg·h/ml on day 1 post treatment, when administered as topical composition once daily for 14 days.

In an aspect, the topical composition of the present application comprising tazarotene provides systemic exposure (mean AUC$_{0-24}$) of tazarotenic acid about 1000 pg·h/ml on day 1 post treatment, when administered as topical composition once daily for 14 days.

In an aspect, the topical composition of the present application comprising tazarotene provides systemic exposure (mean AUC$_{0-24}$) of tazarotenic acid less than about 1400 pg·h/ml on day 7, when administered as topical composition once daily for 14 days.

In an aspect, the topical composition of the present application comprising tazarotene provides systemic exposure (mean AUC$_{0-24}$) of tazarotenic acid about 1275 pg·h/ml on day 7, when administered as topical composition once daily for 14 days.

In an aspect, the topical composition of the present application comprising tazarotene provides systemic exposure (mean AUC$_{0-24}$) of tazarotenic acid less than about 1800 pg·h/ml on day 14, when administered as topical composition once daily for 14 days.

In an aspect, the topical composition of the present application comprising tazarotene provides systemic exposure (mean AUC$_{0-24}$) of tazarotenic acid about 1515 pg·h/ml on day 14, when administered as topical composition once daily for 14 days.

In an aspect, the topical composition of the present application comprising tazarotene provides systemic exposure (mean C$_{max}$) of tazarotenic acid, less than about 160 pg/ml on day 1 post treatment, when administered as topical composition twice daily for 14 days.

In an aspect, the topical composition of the present application comprising tazarotene provides systemic exposure (mean C$_{max}$) of tazarotenic acid, about 110 pg/ml on day 1 post treatment, when administered as topical composition twice daily for 14 days.

In an aspect, the topical composition of the present application comprising tazarotene provides systemic exposure (mean C$_{max}$) of tazarotenic acid, less than about 225 pg/ml on day 7, when administered as topical composition twice daily for 14 days.

In an aspect, the topical composition of the present application comprising tazarotene provides systemic exposure (mean C$_{max}$) of tazarotenic acid, about 150 pg/ml on day 7, when administered as topical composition twice daily for 14 days.

In an aspect, the topical composition of the present application comprising tazarotene provides systemic exposure (mean C$_{max}$) of tazarotenic acid, less than about 315 pg/ml on day 14, when administered as topical composition twice daily for 14 days.

In an aspect, the topical composition of the present application comprising tazarotene provides systemic exposure (mean C$_{max}$) of tazarotenic acid, about 191 pg/ml on day 14, when administered as topical composition twice daily for 14 days.

In an aspect, the topical composition of the present application comprising tazarotene provides systemic exposure (mean C$_{max}$) of tazarotenic acid, less than about 80 pg/ml on day 1 post treatment, when administered as topical composition once daily for 14 days.

In an aspect, the topical composition of the present application comprising tazarotene provides systemic exposure (mean C$_{max}$) of tazarotenic acid, about 62 pg/ml on day 1 post treatment, when administered as topical composition once daily for 14 days.

In an aspect, the topical composition of the present application comprising tazarotene provides systemic exposure (mean C$_{max}$) of tazarotenic acid, less than about 100 pg/ml on day 7, when administered as topical composition once daily for 14 days.

In an aspect, the topical composition of the present application comprising tazarotene provides systemic exposure (mean C$_{max}$) of tazarotenic acid, about 66 pg/ml on day 7, when administered as topical composition once daily for 14 days.

In an aspect, the topical composition of the present application comprising tazarotene provides systemic exposure (mean C$_{max}$) of tazarotenic acid, less than about 95 pg/ml on day 14, when administered as topical composition once daily for 14 days.

In an aspect, the topical composition of the present application comprising tazarotene provides systemic exposure (mean C$_{max}$) of tazarotenic acid, about 80 pg/ml on day 14, when administered as topical composition once daily for 14 days.

In an aspect, the topical composition of the present application comprising tazarotene provides systemic exposure of tazarotenic acid comprising: mean AUC$_{0-24}$ less than about 2600 pg·h/ml and mean C$_{max}$ less than about 160 pg/ml on day 1 post treatment, when administered as topical composition twice daily for 14 days.

In an aspect, the topical composition of the present application comprising tazarotene provides systemic exposure of tazarotenic acid comprising: mean AUC$_{0-24}$ less than about 3900 pg·h/ml and mean C$_{max}$ less than about 230 pg/ml on day 7, when administered as topical composition twice daily for 14 days.

In an aspect, the topical composition of the present application comprising tazarotene provides systemic exposure of tazarotenic acid comprising: mean AUC$_{0-24}$ less than about 5600 pg·h/ml and mean C$_{max}$ less than about 315 pg/ml on day 14, when administered as topical composition twice daily for 14 days.

In an aspect, the topical composition of the present application comprising tazarotene provides systemic exposure of tazarotenic acid comprising: mean AUC$_{0-24}$ about 1690 pg·h/ml and mean C$_{max}$ about 110 pg/ml on day 1 post treatment, when administered as topical composition twice daily for 14 days.

In an aspect, the topical composition of the present application comprising tazarotene provides systemic exposure of tazarotenic acid comprising: mean AUC$_{0-24}$ about 3550 pg·h/ml and mean $C_{max}$ about 150 pg/ml on day 7, when administered as topical composition twice daily for 14 days.

In an aspect, the topical composition of the present application comprising tazarotene provides systemic exposure of tazarotenic acid comprising: mean $AUC_{0-24}$ about 4315 pg·h/ml and mean $C_{max}$ about 190 pg/ml on day 14, when administered as topical composition twice daily for 14 days.

In an aspect, the topical composition of the present application comprising tazarotene provides systemic exposure of tazarotenic acid comprising: mean $AUC_{0-24}$ less than about 1200 pg·h/ml and mean $C_{max}$ less than about 90 pg/ml on day 1 post treatment, when administered as topical composition once daily for 14 days.

In an aspect, the topical composition of the present application comprising tazarotene provides systemic exposure of tazarotenic acid comprising: mean $AUC_{0-24}$ less than about 1550 pg·h/ml and mean $C_{max}$ less than about 90 pg/ml on day 7, when administered as topical composition once daily for 14 days.

In an aspect, the topical composition of the present application comprising tazarotene provides systemic exposure of tazarotenic acid comprising: mean $AUC_{0-24}$ less than about 1800 pg·h/ml and mean $C_{max}$ less than about 100 pg/ml on day 14, when administered as topical composition once daily for 14 days.

In an aspect, the topical composition of the present application comprising tazarotene provides systemic exposure of tazarotenic acid comprising: mean $AUC_{0-24}$ about 980 pg·h/ml and mean $C_{max}$ about 65 pg/ml on day 1 post treatment, when administered as topical composition once daily for 14 days.

In an aspect, the topical composition of the present application comprising tazarotene provides systemic exposure of tazarotenic acid comprising: mean $AUC_{0-24}$ about 1250 pg·h/ml and mean $C_{max}$ about 65 pg/ml on day 7, when administered as topical composition once daily for 14 days.

In an aspect, the topical composition of the present application comprising tazarotene provides systemic exposure of tazarotenic acid comprising: mean $AUC_{0-24}$ about 1515 pg·h/ml and mean $C_{max}$ about 85 pg/ml on day 14, when administered as topical composition once daily for 14 days.

In an aspect, the topical composition of the present application comprising tazarotene, provides percentage ratio of mean $AUC_{0-24}$ of tazarotenic acid between twice daily to once daily administration of topical composition, is from about 120% to 250% with 90% confidence limit on day 1 post treatment of 14 days treatment.

In an aspect, the topical composition of the present application comprising tazarotene, provides percentage ratio of mean $AUC_{0-24}$ of tazarotenic acid between twice daily of topical composition to once daily TAZORAC® cream administration, is from about 45% to 100% with 90% confidence limit on day 1 post treatment of 14 days treatment.

In an aspect, the topical composition of the present application comprising tazarotene provides percentage ratio of mean $AUC_{0-24}$ of tazarotenic acid between once daily of topical composition to once daily TAZORAC® cream administration, is from about 20% to 55% with 90% confidence limit on day 1 post treatment of 14 days treatment.

In an aspect, the topical composition of the present application comprising tazarotene provides percentage ratio of mean $AUC_{0-24}$ of tazarotenic acid between twice daily to once daily administration of topical composition, is from about 200% to 350% with 90% confidence limit on day 7 of 14 days treatment.

In an aspect, the topical composition of the present application comprising tazarotene provides percentage ratio of mean $AUC_{0-24}$ of tazarotenic acid between twice daily to once daily TAZORAC® cream administration of topical composition, is from about 60% to 150% with 90% confidence limit on day 7 of 14 days treatment.

In an aspect, the topical composition of the present application comprising tazarotene provides percentage ratio of mean $AUC_{0-24}$ of tazarotenic acid between once daily to once daily TAZORAC® cream administration of topical composition, is from about 20% to 60% with 90% confidence limit on day 7 of 14 days treatment.

In an aspect, the topical composition of the present application comprising tazarotene provides percentage ratio of mean $AUC_{0-24}$ of tazarotenic acid between once daily to twice daily administration of topical composition, is from about 180% to 350% with 90% confidence limit on day 14 of 14 days treatment.

In an aspect, the topical composition of the present application comprising tazarotene provides percentage ratio of mean $AUC_{0-24}$ of tazarotenic acid between twice daily to once daily TAZORAC® cream administration of topical composition, is from about 40% to 130% with 90% confidence limit on day 14 of 14 days treatment.

In an aspect, the topical composition of the present application comprising tazarotene provides percentage ratio of mean $AUC_{0-24}$ of tazarotenic acid between once daily to once daily TAZORAC® cream administration of topical composition, is from about 20% to 50% with 90% confidence limit on day 14 of 14 days treatment.

In another aspect, twice daily minimum contact time administration of topical composition of the present application comprising tazarotene provides systemic exposure equivalent to that of once-daily TAZORAC® administration.

In another aspect, twice daily minimum contact time administration of topical composition of the present application comprising tazarotene provides systemic exposure equivalent to that of once-daily TAZORAC® cream administration.

In an aspect, the topical composition of the present application comprising tazarotene provides percentage ratio of mean $C_{max}$ of tazarotenic acid between twice daily to once daily administration of topical compositions of present application, is from about 130% to about 250% with 90% confidence limit on day 1 post treatment of 14 days treatment.

In an aspect, the topical composition of the present application comprising tazarotene provides percentage ratio of mean $C_{max}$ of tazarotenic acid between once daily of topical composition to once daily TAZORAC® cream administration, is from about 40% to about 100% with 90% confidence limit on day 1 post treatment of 14 days treatment.

In an aspect, the topical composition of the present application comprising tazarotene provides percentage ratio of mean $C_{max}$ of tazarotenic acid between twice daily of topical composition to once daily TAZORAC® cream administration, is from about 20% to about 60% with 90% confidence limit on day 1 post treatment of 14 days treatment.

In an aspect, the topical composition of the present application comprising tazarotene provides percentage ratio of mean $C_{max}$ of tazarotenic acid between twice daily to once daily administration of topical compositions of present application, is from about 170% to about 280% with 90% confidence limit on day 7 of 14 days treatment.

In an aspect, the topical composition of the present application comprising tazarotene provides percentage ratio of mean $C_{max}$ of tazarotenic acid between once daily of topical composition to once daily TAZORAC® cream administration, is from about 40% to about 120% with 90% confidence limit on day 7 of 14 days treatment.

In an aspect, the topical composition of the present application comprising tazarotene provides percentage ratio of mean $C_{max}$ of tazarotenic acid between twice daily of topical composition to once daily TAZORAC® cream administration, is from about 20% to about 50% with 90% confidence limit on day 7 of 14 days treatment.

In an aspect, the topical composition of the present application comprising tazarotene provides percentage ratio of mean $C_{max}$ of tazarotenic acid between twice daily to once daily administration of topical compositions of present application, is from about 150% to about 300% with 90% confidence limit on day 14 of 14 days treatment.

In an aspect, the topical composition of the present application comprising tazarotene provides percentage ratio of mean $C_{max}$ of tazarotenic acid between once daily of topical composition to once daily TAZORAC® cream administration, is from about 40% to about 90% with 90% confidence limit on day 14 of 14 days treatment.

In an aspect, the topical composition of the present application comprising tazarotene provides percentage ratio of mean $C_{max}$ of tazarotenic acid between twice daily of topical composition to once daily TAZORAC® cream administration, is from about 20% to about 50% with 90% confidence limit on day 14 of 14 days treatment.

In an aspect, the topical composition of the present application comprising tazarotene, provides retinoid activity at par or more than TAZORAC® cream with minimum contact time less than about 5 minutes.

In another aspects, the retinoid activity is correlated to effect on skin barrier function, which is selected from transepidermal water loss or exfoliation.

In another aspect, the topical composition comprising: a) tazarotene; b) an anti-irritant; c) a foaming agent, and d) a pharmaceutically acceptable excipient; wherein said composition provides retinoid activity at application site with minimum period of contact time, and said minimum period of contact time is less than about 5 minutes.

In an aspect, the topical composition comprising: a) tazarotene; b) an anti-irritant selected from polyhydroxy acids; c) a foaming agent selected from disodium laureth sulfosuccinate, cocobetaine, sodium lauryl sarcosinate, and sodium lauryl sulfate, and d) a pharmaceutically acceptable excipient; wherein said composition provides required retinoid activity at application site with minimum period of contact time, and said minimum period of contact time is less than about 5 minutes.

In an aspect, the topical composition of the present application comprising tazarotene with minimum contact time less than about 5 minutes, provides retinoid activity; wherein the retinoid activity is increased transepidermal water loss as compared to day 1 (baseline).

In another aspect, the transepidermal water loss increased at least about 5% as compared to day 1 (baseline).

In another aspect, the transepidermal water loss increased at least about 10% as compared to day 1 (baseline).

In another aspect, the transepidermal water loss increased at least about 15% as compared to day 1 (baseline).

In another aspect, the transepidermal water loss increased at least about 20% as compared to day 1 (baseline).

In another aspect, the transepidermal water loss increased at least about 30% as compared to day 1 (baseline).

In an aspect, the topical composition of the present application comprising tazarotene with minimum contact time less than about 5 minutes, provides retinoid activity; wherein the retinoid activity is increased exfoliation compared to day 1 (baseline).

In an aspect, the topical composition of the present application comprising tazarotene with minimum contact time less than about 5 minutes, provides retinoid activity; wherein the retinoid activity increases transepidermal water loss compared to TAZORAC® gel.

In an aspect, the topical composition of the present application comprising tazarotene with minimum contact time less than about 5 minutes, provides retinoid activity; wherein the retinoid activity increases exfoliation compared to TAZORAC® gel.

EXAMPLES

The following examples are provided to illustrate certain specific aspects of the invention, and should not be construed to limit the scope of the invention in any manner. The following examples may include compilations of data that are representative of data gathered at various times during the course of development and experimentation related to the present invention.

In the examples, particle size of tazarotene was either D90≈10 μm or ≈50 μm.

Examples for retinoid-containing topical compositions:

Example 1

| Ingredients | % w/w |
| --- | --- |
| Tazarotene | 0.1 |
| Sodium lauryl sulfate | 1.0 |
| Stearyl alcohol | 2.0 |
| Cetyl alcohol | 1.2 |
| Gluconolactone | 0.25 |
| Glycerin | 4.0 |
| Tocofersolan | 0.5 |
| Carbopol 971P | 0.25 |
| Propyl paraben | 0.03 |
| Methyl paraben | 0.20 |
| Edetate disodium | 0.1 |
| Butylated Hydroxy Toluene | 0.05 |
| Caprylic/Capric Triglyceride | 3.5 |
| Triethanolamine | q.s. to pH 6.3 |
| Purified water | q.s. to 100 |

Process of Preparation:

Preparation of aqueous phase: An aqueous phase was prepared initially by adding together, a sufficient quantity of purified water, glycerin, methyl paraben, galaconolactone, and edetate disodium, under stirring to prepare a clear dispersion. Further, carbopol 971P was added to this dispersion under homogenization, and further,—sodium lauryl sulfate, at a concentration of around 90%, was added to this dispersion under homogenization, and the temperature of the contents was maintained at 70±5° C.

Preparation of oil phase: An oil phase was prepared by mixing stearyl alcohol, cetyl alcohol, caprylic/capric triglyceride, and tocofersolan, and these ingredients were melted and stirred well, and further, propyl paraben and butylated hydroxyl toluene were added to the above dispersion. Temperature of the contents was maintained 70±5° C. throughout the process. This oil phase was mixed slowly with aqueous phase under homogenization to prepare the emulsion, and cooled down to 30±2° C. The pH of the emulsion was adjusted to 5.2±0.2 by adding triethanolamine under homogenization.

Drug dispersion was prepared by adding tazarotene and remainder of sodium lauryl sulfate to sufficient quantity of purified water, by stirring. This drug dispersion was mixed with the emulsion under homogenization. The pH of the product was then adjusted to 6.3±0.2 by adding triethanolamine solution, and the final weight is made up with purified water.

Example 2

| Ingredients | % w/w |
|---|---|
| Tazarotene | 0.1 |
| Sodium Lauryl Sulfate | 1.0 |
| Stearyl alcohol | 2.5 |
| Cetyl alcohol | 1.5 |
| Gluconolactone | 0.25 |
| Glycerin | 4.0 |
| Tocofersolan | 0.5 |
| Carbopol 980 | 0.75 |
| Propyl paraben | 0.2 |
| Methyl paraben | 0.2 |
| Triethanolamine | q.s. to pH 6.3 |
| Purified water | q.s. to 100 |

Process of Preparation:

Preparation of aqueous phase: An aqueous phase was prepared initially by adding together, a sufficient quantity of purified water, glycerin, methyl paraben, glucaonolactone, and edetate disodium under stirring to prepare a clear dispersion. Further, carbopol 980 was added to this dispersion under homogenization, and further, sodium lauryl sulfate, at a concentration of around 90%, was added to this dispersion under homogenization. The temperature of the contents was maintained at 70±5° C.

Preparation of oil phase: An oil phase was prepared by mixing stearyl alcohol, cetyl alcohol, tocofersolan, and these ingredients were melted and stirred well, and further, propyl paraben was added to the above dispersion. The temperature of the contents was maintained at 70±5° C. throughout the process. This oil phase was mixed slowly with the aqueous phase under homogenization to prepare the emulsion, and cooled down to 30±2° C. The pH of this emulsion was adjusted to 5.2±0.2 by adding triethanolamine under homogenization.

Drug dispersion was prepared by adding tazarotene and remainder of sodium lauryl sulfate to sufficient quantity of purified water, by stirring. This drug dispersion was mixed with emulsion under homogenization. The pH of the product was then adjusted to 6.3±0.2 by adding triethanolamine solution, and the final weight is made up with purified water.

Example 3

| Ingredients | Example 3A % w/w | Example 3B % w/w | Example 3C % w/w |
|---|---|---|---|
| Tazarotene | 0.10 | 0.10 | 0.10 |
| Disodium Laureth Sulfosuccinate | 2.00 | — | — |
| Cocobetaine | 3.00 | 3.00 | — |
| Sodium Lauroyl Sarcosinate | — | 2.00 | — |
| Sodium Lauryl Sulfate | — | — | 1.00 |
| Stearyl Alcohol | 2.00 | 2.00 | — |
| Cetyl Alcohol | 1.20 | 1.20 | — |
| Gluconolactone | 0.25 | 0.25 | 0.25 |
| Tocofersolan | 0.50 | 0.50 | 0.50 |
| Glycerine | 4.00 | 4.00 | 4.00 |
| Carbomer 971 P | 0.75 | 0.75 | 0.75 |
| Propyl Paraben | 0.03 | 0.03 | 0.20 |
| Methyl Paraben | 0.20 | 0.20 | 0.20 |
| Disodium Edetate | 0.10 | 0.10 | 0.10 |
| Butylated Hydroxy Toluene | 0.05 | 0.05 | 0.05 |
| Caprylic/Capric Triglyceride | 2.00 | 2.00 | — |
| Triethanolamine | q.s. to pH 6.3 | q.s. to pH 6.3 | q.s. to pH 6.3 |
| Purified Water | q.s. to 100 | q.s. to 100 | q.s. to 100 |
| Total | 100.00 | 100.00 | 100.00 |

Process of Preparation:

Preparation of aqueous phase: An aqueous phase was prepared initially by adding together, a sufficient quantity of purified water, glycerin, methyl paraben, gluconolactone, and edetate disodium, under stirring to prepare a clear dispersion. Further, carbopol 971 P was added to this dispersion under homogenization, and further, a foaming agent (either sodium lauryl sulfate, or sodium lauroyl sarcosinate and cocobetaine, or disodium laureth sulfosuccinate and cocobetaine), at a concentration of around 90%, was added to this dispersion under homogenization. The temperature of the contents was maintained at 70±5° C.

Preparation of oil phase: An oil phase was prepared by mixing stearyl alcohol, cetyl alcohol, and tocofersolan, and these ingredients were melted at 70° C. and stirred, and further, propyl paraben was added to the above dispersion. The temperature of the ingredients was maintained at 70±5° C. throughout this process. This oil phase was mixed slowly with the aqueous phase under homogenization to prepare the emulsion, and cooled down to 30±2° C. The pH of this emulsion was adjusted to 5.2±0.2 by adding triethanolamine under homogenization.

Drug dispersion was prepared by adding tazarotene and remainder of sodium lauryl sulfate to sufficient quantity of purified water, by stirring. This drug dispersion was mixed with the emulsion under homogenization. The pH of the product was then adjusted to 6.3±0.2 by adding triethanolamine solution and the final weight is made up with purified water.

Example 4: Rat Skin Affinity Study

The retinoid-containing topical composition of the present application shows skin deposition of retinoid compound and skin affinity, in rat skin flap study. The rat skin flap study reveals that the retinoid-containing topical composition of the present application exhibits more skin affinity and therefore provides desired retinoid compound deposition in the skin.

Rat skin affinity study protocol:

This protocol was used to examine the influence of retinoid-containing topical compositions on skin affinity. Study design and procedures were as follows:

The skin flaps of 50 cm$^2$ (10 cm×5 cm) from dorsal surface of SD/wistar rats were taken for each composition. The weight of each skin flap also was recorded.

Total four retinoid-containing topical compositions were evaluated. Total twelve skin flaps for four compositions (three skin flaps per composition). Total four skin flaps for four placebo compositions.

Application procedure: 10 ml of the composition (active/placebo) was taken and 10 ml demineralized water was added to it and mixed well to make lather and spread on the skin, and immediately, this was washed off with 100 ml of demineralized water. This procedure was repeated as follows: 2 applications in first flap; 14 applications in second flap; 28 applications in third flap; and fourth flap was for placebo composition. In case of placebo composition, visual observation was made after 2, 14, and 28 application-washing cycles.

Observation: After completion of the study, the applied skin flaps were visually inspected for changes in color and texture in both drug and placebo treated skin flaps. An area of 4 cm$^2$ of skin pieces was separated from each skin flaps after subsequent washes of 2, 14, 28, and each skin flap was analyzed, and concentration of tazarotene was quantified by a sensitive UPLC/HPLC method. The skin pieces were evaluated for deposition of tazarotene in skin pores.

TABLE 1

Effect of Number of washes Vs. Tazarotene deposition in skin

| Examples | No. of washes | Tazarotene deposited (μg)/gm of skin |
|---|---|---|
| Example 1 | 2 | 20.48 |
|  | 14 | 31.14 |
|  | 28 | 44.11 |
| Example 3A | 2 | 26.11 |
|  | 14 | 21.98 |
|  | 28 | 16.01 |
| Example 3B | 2 | 6.94 |
|  | 14 | 15.94 |
|  | 28 | 21.45 |
| Example 3C | 2 | 19.81 |
|  | 14 | 33.08 |
|  | 28 | 35.12 |

In table 1, Example 1 and Example 3C were showing more skin tazarotene deposition and continuous increase in tazarotene deposition with increase in number of washes, while Example 3A and 3B were showing less tazarotene deposition. Example 1 showed linear increase in tazarotene deposition, whereas Example 3C showed drug deposition rate flat after 14 wash. In case of Example 3A, tazarotene dislodging occurred because of cleansing effect of the composition. In other words, Example 1 and 3C showed more skin deposition of tazarotene in the skin.

Example 5: Two Weeks Skin Deposition Study in Neonatal Minipigs

Six neonatal minipigs were selected and the hair on the back of the animals were clipped and divided into ten portions (4 cm×3 cm), and were wiped clean with water. All the animals were anesthetized and the treatments were applied over an area of 12 cm$^2$ within 15 seconds per massage. All the applied areas were rinsed off with 20 ml of water after 5 minutes of the application. The skin was then scored for visual appearance, erythema and edema before application and after 1 h of removal of composition (followed by Draize system of scoring). The same treatment/irritancy scoring was repeated every 24 hours for two weeks. After completion of the two weeks treatment cycle, the treated skin was excised till subcutaneous fat and the skin was further split into dermis and epidermis layers, and was transferred into the extraction solvent. The tissue was then homogenized and tazarotene was extracted. After centrifugation of the sample to remove the cellular debris, the supernatant was analyzed for tazarotene and its metabolite tazarotenic acid.

Each composition of Example 1 and Examples 3A, 3B and 3C were prepared with two different particle sizes D90 is 10 μm and 50 μm, and they were called fraction 1 and fraction 2 respectively.

TABLE 2

The treatment groups are divided as follows:

| Codes | Treatment groups | Tazarotene particle size (μm) |
|---|---|---|
| F1-1 | Fraction1_Example 1 | 10 |
| F2-1 | Fraction2_Example 1 | 50 |
| F1-3A | Fraction1_Example 3A | 10 |
| F2-3A | Fraction2_Example 3A | 50 |
| F1-3B | Fraction1_Example 3B | 10 |
| F2-3B | Fraction2_Example 3B | 50 |
| F1-3C | Fraction1_Example 3C | 10 |
| F2-3C | Fraction2_Example 3C | 50 |
| Placebo | Control | — |
| Reference | TAZORAC gel | — |

TABLE 3

Percentage retention of Tazarotene and its metabolite in epidermis (E) and dermis (D)

| Compositions | Tazarotene (E) | Tazarotene (D) | Combined (E + D) Tazarotene | Tazarotenic acid (E) | Tazarotenic acid (D) | Combined (E + D) Tazarotenic acid |
|---|---|---|---|---|---|---|
| F1-1 | 0.63 | 0.13 | 0.76 | 0.12 | 0.05 | 0.17 |
| F2-1 | 0.70 | 0.15 | 0.85 | 0.13 | 0.03 | 0.16 |
| F1-3A | 0.85 | 0.41 | 1.26 | 0.16 | 0.21 | 0.36 |
| F2-3A | 0.27 | 0.07 | 0.34 | 0.1 | 0.07 | 0.16 |
| F1-3B | 0.9 | 0.11 | 1.02 | 0.05 | 0.05 | 0.10 |
| F2-3B | 0.35 | 0.09 | 0.44 | 0.07 | 0.02 | 0.09 |
| F1-3C | 0.44 | 0.31 | 0.75 | 0.06 | 0.03 | 0.09 |
| F2-3C | 0.35 | 0.06 | 0.41 | 0.08 | 0.01 | 0.09 |
| TAZORAC | 0.51 | 0.12 | 0.63 | 0.27 | 0.07 | 0.34 |

All the compositions showed similar tazarotene depositions in epidermis and dermis which were equivalent or more than reference product. Both fraction 1 and fraction 2 of example 1 exhibited comparable skin retention.

Tazarotene forms tazarotenic acid in dermis layer. Tazarotenic acid is believed to cause irritation to the skin. Epidermal degradation of tazarotene was lesser in the present topical compositions than the reference product (TAZORAC). Thus all the compositions of the present application provide higher skin retention and lesser irritation to the skin.

Example 6: Skin Irritancy Study

The skin irritancy characteristics were evaluated by Draize test and the evaluation was performed on all the compositions listed in table 2. In Draize test, skin irritation was visually evaluated based on appearance and severity of erythema, and all the treatment sites were also evaluated microscopically.

Tazarotene of all the treatment groups had caused erythema. The severity was lesser on the day 3 which then progressed to moderate erythema from the days 6-8 and reversed to slight erythema from the days 9-14. There was no obvious difference in skin irritation pattern between all the treatment groups.

Example 7: Stability Studies

The prepared composition of example 1 was filled into closed container and exposed to the stability testing conditions 25° C. and 60% relative humidity (RH), 30° C. and 65% RH, and 40° C. and 75% RH for nine months, and analyses at various storage points are shown in Table 4.

TABLE 4

Stability testing of Example 1

| Storage Condition Acceptance criteria | Assay 90.0-110.0% | Content Uniformity $ | Imp A NMT 1.0% | Imp B NMT 1.0% | Imp C NMT 1.0% | SMI NMT 0.5% | Total Impurities NMT 5.0% | Viscosity # | pH 4.0-7.0 |
|---|---|---|---|---|---|---|---|---|---|
| Initial | 101.2 | Top-101.7 Middle-100.9 Bottom-100.9 % RSD-0.45 | ND | 0.18 | ND | ND | 0.18 | 7048 | 5.99 |
| 1 M 25° C./60% RH | 99.5 | Top -99.4 Middle -99.2 Bottom -99.9 % RSD-0.36 | ND | 0.25 | ND | ND | 0.31 | 6509 | 5.88 |
| 1 M 40° C./75% RH | 99.0 | Top -98.9 Middle -99.0 Bottom -99.1 % RSD-0.10 | ND | 0.34 | ND | ND | 0.34 | 6719 | 5.86 |
| 2 M 25° C./60% RH | 98.7 | NA | ND | 0.28 | ND | ND | 0.28 | 7228 | 5.95 |
| 2 M 40° C./75% RH | 98.1 | NA | ND | 0.37 | ND | ND | 0.37 | 6599 | 5.90 |
| 3 M 25° C./60% RH | 101.2 | Top -101.7 Middle -101.0 Bottom -101.0 % RSD-0.40 | ND | 0.45 | ND | ND | 0.45 | 6449 | 5.93 |
| 3 M 30° C./65% RH | 100.5 | Top -100.5 Middle -100.6 Bottom -100.3 % RSD-0.15 | ND | 0.30 | ND | ND | 0.30 | 7348 | 5.97 |
| 3 M 40° C./75% RH | 98.9 | Top -98.5 Middle -99.0 Bottom -99.1 % RSD-0.33 | ND | 0.64 | ND | ND | 0.64 | 6419 | 5.92 |
| 6 M 25° C./60% RH | 98.5 | Top -98.7 Middle -98.3 Bottom -98.5 % RSD-0.2 | ND | 0.48 | ND | ND | 0.48 | 5969 | 5.96 |
| 6 M 30° C./65% RH | 97.5 | Top -97.5 Middle -97.5 Bottom -97.4 % RSD-0.1 | ND | 0.49 | ND | ND | 0.49 | 4969 | 5.92 |
| 6 M 40° C./75% RH | 96.5 | Top -96.4 Middle -96.6 Bottom -96.6 % RSD-0.1 | ND | 0.69 | ND | ND | 0.69 | 4169 | 5.85 |
| 9 M 25° C./60% RH | 101.1 | NA | ND | 0.86 | ND | ND | 0.86 | 4409 | 5.87 |
| 9 M 30° C./65% RH | 99.0 | NA | ND | 0.88 | ND | ND | 0.88 | 3989 | 5.85 |

TABLE 4-continued

Stability testing of Example 1

| Storage Condition Acceptance criteria | Assay 90.0-110.0% | Content Uniformity $ | Imp A NMT 1.0% | Imp B NMT 1.0% | Imp C NMT 1.0% | SMI NMT 0.5% | Total Impurities NMT 5.0% | Viscosity # | pH 4.0-7.0 |
|---|---|---|---|---|---|---|---|---|---|
| 12 M 25° C./60% RH | 95.9 | Top-97.6 Middle-97.9 Bottom-98.0 RSD-0.2 | ND | 0.51 | ND | ND | 0.51 | 4679 | 5.79 |
| 12 M 30° C./65% RH | 95.9 | Top-99.8 Middle-99.7 Bottom-99.2 RSD-0.3 | ND | 0.57 | ND | ND | 0.57 | 4229 | 5.83 |

ND—Not detected,
SMI—Single major unknown impurity
NA—Not Applicable,
: - For Information
$: - The content of each sample is between 90-110% of the label claim.
RSD of sample should not exceed 6%.

Example 8: Microscopy Data for Example 1

The compositions of Example 1 was examined by preparing 5% solution of Triton ×100 in purified water. The composition was dispersed in dispersion media, and the dispersion was measured for its particle size and globule size.

TABLE 5

Microscopic observation of Example 1

| | Particle size of Tazarotene | | | Globule size of oil Phase | | |
|---|---|---|---|---|---|---|
| Condition | D10 | D50 | D90 | D10 | D50 | D90 |
| Initial (batch 1) | 3.5 | 4.3 | 8.2 | 3.4 | 5.5 | 8.7 |
| Initial (batch 2) | 4.2 | 5.4 | 15.0 | 4.1 | 6.2 | 8.9 |
| Initial (batch 3) | 3.8 | 4.9 | 12.3 | 3.5 | 5.4 | 8.3 |
| Initial (batch 4) | 3.8 | 5.7 | 12.9 | 3.9 | 6.0 | 8.8 |
| Initial (batch 5) | 3.8 | 6.1 | 14.2 | 3.8 | 5.7 | 8.9 |
| 24 M 25° C./60% RH | 2.3 | 6.6 | 16.2 | 2.0 | 3.0 | 4.8 |

Example 9: Excipients Compatibility Study with Tazarotene

Excipient compatibility study for tazarotene was carried out with various pharmaceutically acceptable excipients. The tazarotene was tested in a set of compatibility screening studies with the excipients in closed vials containing tazarotene. The excipients physical mixture were incubated in ovens with and without moisture at 60° C. or 40° C./75% RH for 4 weeks.

Conclusion:

The result of the excipient compatibility study had shown that tazarotene was incompatible with benzyl alcohol, lactic acid, polysorbate 80. Tazarotene is compatible with excipients of examples 1, 2, 3 such as carbomer polymer type A and type B, cocobetaine, sodium lauryl sarcosinate, stearyl alcohol, cetyl alcohol, glycerine, vitamin E TPGS, gluconolactone, butylated hydroxytoluene, propylparaben, and methylparaben.

TABLE 6A

Initial excipients compatibility

| S. No | Drug/Excipient | Imp-A | Imp-B | Imp-C | SMI | Total imp |
|---|---|---|---|---|---|---|
| 1. | Tazarotene + Lactic acid (0.1:18) | ND | 0.30 | 0.09 | 0.07 | 0.50 |
| 2. | Tazarotene + Lactic acid (0.1:9) | ND | 0.24 | 0.05 | 0.04 | 0.34 |
| 3. | Tazarotene + Oleic acid (0.1:25) | ND | 1.00 | ND | 0.05 | 1.05 |
| 4. | Tazarotene + Oleic acid (0.1:12.5) | ND | 1.00 | ND | 0.05 | 1.05 |
| 5. | Tazarotene + Isostearic acid (0.1:25) | ND | 0.79 | ND | ND | 0.79 |
| 6. | Tazarotene + Isostearic acid (0.1:12.5) | ND | 1.23 | ND | ND | 1.23 |
| 7. | Tazarotene + Benzyl alcohol (0.1:2.7) | ND | 3.84 | ND | ND | 3.84 |
| 8. | Tazarotene + Benzyl alcohol (0.1:1.35) | ND | 1.84 | ND | ND | 1.84 |
| 9. | Tazarotene + Propylene Glycol (0.1:20) | ND | 0.43 | ND | ND | 0.43 |
| 10. | Tazarotene + Propylene Glycol (0.1:10) | ND | 0.76 | ND | ND | 0.76 |
| 11. | Tazarotene + Polysorbate 80 (0.1:15) | ND | 0.30 | 0.09 | 0.07 | 0.50 |
| 12. | Tazarotene + Polysorbate 80 (0.1:7.5) | ND | 0.24 | 0.05 | 0.04 | 0.34 |

TABLE 6B

Excipients compatibility at 4 weeks 40° C./75% RH

| S. No | Drug/Excipient | Imp-A | Imp-B | Imp-C | SMI | Total imp |
|---|---|---|---|---|---|---|
| 1. | Tazarotene + Lactic acid (0.1:18) | 0.13 | 0.85 | 0.83 | 3.18 | 12.18 |
| 2. | Tazarotene + Lactic acid (0.1:9) | 0.07 | 0.54 | 0.39 | 1.98 | 7.66 |
| 3. | Tazarotene + Oleic acid (0.1:25) | ND | 1.98 | ND | ND | 1.98 |
| 4. | Tazarotene + Oleic acid (0.1:12.5) | ND | 4.16 | 0.06 | 0.25 | 4.47 |
| 5. | Tazarotene + Isostearic acid (0.1:25) | ND | 4.69 | 0.05 | ND | 4.74 |
| 6. | Tazarotene + Isostearic acid (0.1:12.5) | ND | 2.59 | 0.07 | ND | 2.66 |
| 7. | Tazarotene + Benzyl alcohol (0.1:2.7) | | High degradation | | | |
| 8. | Tazarotene + Benzyl alcohol (0.1:1.35) | | | | | |
| 9. | Tazarotene + Propylene Glycol (0.1:20) | ND | 0.95 | ND | 0.23 | 1.27 |
| 10. | Tazarotene + Propylene Glycol (0.1:10) | ND | 1.54 | 0.21 | 0.11 | 1.87 |
| 11. | Tazarotene + Polysorbate 80 (0.1:15) | ND | 31.45 | ND | 0.17 | 31.75 |
| 12. | Tazarotene + Polysorbate 80 (0.1:7.5) | ND | 14.38 | ND | 0.06 | 14.44 |

TABLE 6C

Excipients compatibility at 4 weeks 60° C.

| S. No | Drug/Excipient | Imp-A | Imp-B | Imp-C | SMI | Total imp |
|---|---|---|---|---|---|---|
| 1. | Tazarotene + Lactic acid (0.1:18) | 0.36 | 0.84 | 0.63 | 11.34 | 87.78 |
| 2. | Tazarotene + Lactic acid (0.1:9) | 0.35 | 2.11 | 0.65 | 24.85 | 76.68 |
| 3. | Tazarotene + Oleic acid (0.1:25) | ND | 20.87 | 0.12 | 1.10 | 22.61 |
| 4. | Tazarotene + Oleic acid (0.1:12.5) | ND | 20.98 | 0.13 | 1.12 | 22.36 |
| 5. | Tazarotene + Isostearic acid (0.1:25) | ND | 16.93 | 0.13 | 0.43 | 17.60 |
| 6. | Tazarotene + Isostearic acid (0.1:12.5) | ND | 11.59 | 0.13 | 0.54 | 12.69 |
| 7. | Tazarotene + Benzyl alcohol (0.1:2.7) | | High degradation | | | |
| 8. | Tazarotene + Benzyl alcohol (0.1:1.35) | | | | | |
| 9. | Tazarotene + Propylene Glycol (0.1:20) | ND | 2.95 | ND | 1.66 | 5.58 |
| 10. | Tazarotene + Propylene Glycol (0.1:10) | ND | 2.96 | ND | 1.64 | 5.57 |
| 11. | Tazarotene + Polysorbate 80 (0.1:15) | ND | 61.34 | ND | 0.73 | 62.49 |
| 12. | Tazarotene + Polysorbate 80 (0.1:7.5) | ND | 75.40 | ND | 2.76 | 78.79 |

Example 10: Foaming Capacity Study

Compositions of Example 1, and Examples 3A, 3B, and 3C were evaluated for foaming capacity. 5 gm of the compositions of Example 1 and Examples 3A, 3B, and 3C each were taken in a separate 100 ml glass beakers, and 10 ml of purified water was added to the beakers. The content of the beakers was allowed to stand for 30 minutes. The content of the beakers was stirred with a glass rod. The dispersion/slurry was transferred to a 250 ml measuring cylinder and no foam was produced while transferring the content. The volume was adjusted up to 50 ml of the measuring cylinder by adding water, and the contents of the cylinder was brought to 30° C. After the contents reached 30° C., the contents were given 12 complete shake. The shake action was performed as measuring cylinder was closed and inverted to 180 degree down and restored back to normal position. This shake action was performed 12 times. After the shake, the contents were allowed to stand for 5 minutes. The foam capacity was calculated as follows: a) foam plus water ($V_1$ ml), and b) water only ($V_2$ ml). The foaming capacity is in ml=$V_1$-$V_2$.

Results:

The foam generated for example 1 was in the range of 10 ml to 34 ml, in case of example 3A, 3B, and 3C compositions provided 10 ml to 102 ml of foam. The high foaming capacity was seen in example 3C which provided 103 ml of foam.

Example 11: Tazarotene Composition and Study on Stability of Tazarotene in Different pH

| S. No | Ingredients | % w/w |
|---|---|---|
| 1. | Tazarotene | 0.10 |
| 2. | Sodium Lauryl Sulfate | 1.00 |
| 3. | Gluconolactone | 0.25 |
| 4. | Tocofersolan | 0.50 |
| 5. | Glycerine | 4.00 |
| 6. | Carbomer 971 P | 0.75 |
| 7. | Propyl Paraben | 0.20 |
| 8. | Methyl Paraben | 0.20 |
| 9. | Disodium Edetate | 0.10 |
| 10. | Butylated Hydroxy Toluene | 0.05 |
| 11. | Caprylic/Capric Triglyceride | 2.0 |
| 12. | Triethanolamine | q.s. |
| 13. | Purified Water | q.s. to 100 |
| | Total | 100.00 |

Manufacturing Process:

The above composition was prepared by a process denoted in example 1 till emulsification. The emulsified base was neutralized to following pH:

| Emulsified base | pH of emulsified base (pre-neutralization) | pH of the composition |
|---|---|---|
| Part 1 | 3.2 | 3.01 |
| Part 2 | 4.65 | 4.59 |

-continued

| Emulsified base | pH of emulsified base (pre-neutralization) | pH of the composition |
|---|---|---|
| Part 3 | 5.45 | 5.26 |
| Part 4 | 6.39 | 6.31 |

Tazarotene phase was added separately to these four parts of emulsified base and homogenized as mentioned in Example 1 process and pH of the composition was adjusted. The composition was evaluated for stability for about 2 months.

TABLE 7

Stability results of Example 11

| Composition | Condition | Related substances (RS) | % RS |
|---|---|---|---|
| Composition of Part 1 | Initial | Impurity A | ND |
| | | Impurity B | 0.49 |
| | | Impurity C | ND |
| | | SMI | ND |
| | | Total impurities | 0.49 |
| | 2 months, 45° C. | Impurity A | 0.22 |
| | | Impurity B | 1.62 |
| | | Impurity C | 1.25 |
| | | SMI | 1.46 |
| | | Total impurities | 8.81 |
| Composition of Part 2 | Initial | Impurity A | ND |
| | | Impurity B | 0.33 |
| | | Impurity C | ND |
| | | SMI | ND |
| | | Total impurities | 0.33 |
| | 2 months, 45° C. | Impurity A | 0.01 |
| | | Impurity B | 0.38 |
| | | Impurity C | 0.06 |
| | | SMI | 0.05 |
| | | Total impurities | 0.52 |
| Composition of part 3 | Initial | Impurity A | ND |
| | | Impurity B | 0.24 |
| | | Impurity C | ND |
| | | SMI | ND |
| | | Total impurities | 0.24 |
| | 2 months, 45° C. | Impurity A | 0.01 |
| | | Impurity B | 0.38 |
| | | Impurity C | 0.03 |
| | | SMI | ND |
| | | Total impurities | 0.52 |
| Composition of Part 4 | Initial | Impurity A | ND |
| | | Impurity B | 0.24 |
| | | Impurity C | ND |
| | | SMI | ND |
| | | Total impurities | 0.24 |
| | 2 months, 45° C. | Impurity A | 0.01 |
| | | Impurity B | 0.41 |
| | | Impurity C | 0.08 |
| | | SMI | 0.08 |
| | | Total impurities | 0.66 |

Physical Observation:

The Composition of part 1, 2, 3 and 4 were observed to be complete yellow, off white, white and white respectively at 2 months, 45° C. The final composition of part 3 and 4 were finalized due its physical and chemical stability.

Example 12: Multiple Dose Bioavailability Study of Tazarotene Composition 0.1% of Example 1 Versus TAZORAC® 0.1% Cream Study design: The study was a single-center, randomized, multiple dose, laboratory-blinded, open-label, 3-arm, parallel design in healthy male subjects. The following investigational products were to be administered: 1) Test product: composition of example 1 (tazarotene 0.1%) and 2) reference: TAZORAC cream 0.1%. Following were treatment arms: 1) Treatment 1: Test product applied twice daily, in the morning and evening, 12 hours apart; 2) Treatment 2: Test product applied once daily, in the morning; and 3) Treatment 3: Reference product applied once daily, in the morning. For each study arm (n=16), approximately 5 g of the Test or Reference product was to be applied to the subjects face, neck, shoulders, upper chest and upper back (total approximately equivalent to 15% body surface area (BSA)) over 14 consecutive days (Days 1 to 14). Blood sample were collected time to time as per the schedule of the study.

Conclusion: Very low concentrations of the parent compound, tazarotene, were detected in plasma samples. Following topical application, tazarotene undergoes rapid esterase hydrolysis to its primary active metabolite, tazarotenic acid, and typically little parent compound is detected in plasma.

The exposure to tazarotenic acid was more than 2 times higher when the example 1 composition was applied as a lotion twice daily (Treatment-1) compared to a once daily application (Treatment-2). This indicates linear pharmacokinetics between once a day versus twice a day application.

It appears that following multiple applications of the example 1 composition, the exposure ($AUC_{0-24}$) to tazarotenic acid could be similar when compared to the multiple applications of the cream.

TABLE 8

Summary of plasma tazarotenic acid pharmacokinetic parameters day 1

| Parameters (units) | Treatment 1 | | Treatment 2 | | Treatment 3 | |
|---|---|---|---|---|---|---|
| | Mean | Coefficient variation (CV) % | Mean | Coefficient variation (CV) % | Mean | Coefficient variation (CV) % |
| Mean $C_{max}$ (pg/ml) | 108 | 30.4 | 63 | 58.8 | 159 | 38.2 |
| $T_{max}$ (hours) | 18 | 1-23.92 | 12 | 1-23.92 | 12 | 8-11.92 |
| Mean $AUC_{0-12}$ (pg · h/ml) | 548 | 43.7 | NA | NA | NA | NA |
| Mean $AUC_{0-24}$ (pg · h/ml) | 1688 | 31.9 | 978 | 42.5 | 2546 | 36.2 |

NA: Not applicable

TABLE 9

Summary of Plasma Tazarotenic acid pharmacokinetic parameters-Day 7

| Parameters (units) | Treatment 1 | | Treatment 2 | | Treatment 3 | |
|---|---|---|---|---|---|---|
| | Mean | Coefficient variation (CV) % | Mean | Coefficient variation (CV) % | Mean | Coefficient variation (CV) % |
| Mean $C_{max}$ (pg/ml) | 150 | 41.2 | 66 | 24.4 | 225 | 68.7 |
| $T_{max}$ (hours) | 8 | 4-11.92 | 8 | 6-11.92 | 8 | 5.92-11.95 |
| Mean $AUC_{0-12}$ (pg · h/ml) | 1644 | 40.6 | NA | NA | NA | NA |
| Mean $AUC_{0-24}$ (pg · h/ml) | 3512 | 39.6 | 1270 | 25.3 | 3875 | 57.7 |

NA: Not applicable

TABLE 10

Summary of Plasma Tazarotenic acid pharmacokinetic parameters-Day 14

| Parameters (units) | Treatment 1 | | Treatment 2 | | Treatment 3 | |
|---|---|---|---|---|---|---|
| | Mean | Coefficient variation (CV) % | Mean | Coefficient variation (CV) % | Mean | Coefficient variation (CV) % |
| Mean $C_{max}$ (pg/ml) | 191 | 65.9 | 79 | 20.1 | 313 | 63.5 |
| $T_{max}$ (hours) | 5 | 0-8.0 | 8 | 2-11.92 | 8 | 6-12 |
| Mean $AUC_{0-12}$ (pg · h/ml) | 2038 | 63.2 | NA | NA | NA | NA |
| Mean $AUC_{0-24}$ (pg · h/ml) | 4312 | 58.3 | 1515 | 17.2 | 5408 | 56.8 |

NA: Not applicable

Example 13: Comparison of TAZORAC (Tazarotene 0.1%) Gel to Example 1, on Changes in Transepidermal Water Loss on the Face Twenty-four (24) subjects were enrolled into this study. Example 1, 0.1% and Vehicle (Placebo) composition were applied twice daily to test sites on the subject's face. The Example 1 composition and Vehicle composition were removed after 1 minute with water dampened cotton balls. TAZORAC® gel, 0.1% was applied once daily and removed after 5 minutes with water dampened cotton balls. The study product application was repeated for 21 consecutive days.

The forehead sites received the TAZORAC® gel and Example 1 (one side each), one cheek received the Vehicle Lotion and the other cheek served as an untreated control. Test sites were treated with 2.5 uL/cm² of study product. Subjects washed their face with Cetaphil Daily Facial Cleanser twice daily, not less than 60 minutes prior to test site evaluations. All test sites were assessed for transepidermal water-loss (TEWL) using an evaporimeter and visually scored for exfoliation in the morning before study product application.

Transepidermal water loss score: TEWL at the treated sites was measured once daily in the morning before study product application and at least 60 minutes after any face washing.

Exfoliation score: Test sites were scored once daily for exfoliation (scored as 0=none, 1=scaling/peeling in a small portion of the test site, 2=up to one-half of the site peeling or having peeled, 3=over one half of the site peeling or having peeled). Across all products, mean daily scores ranged from 0 to 0.2. The daily scores were summed for a total score for each subject and study products compared.

Conclusion: Upon topical treatment with many retinoids, a physiological change occurs in the stratum corneum exfoliation process leading to a reduction in its barrier properties as evidenced by increased TEWL (Lehman, 2013). Often accompanying this increase in TEWL is transient accelerated exfoliation (e.g. peeling) and mild irritation. Based on the results of this study, Example 1 appeared to have significant retinoid activity when applied to the forehead for 1 minute and then wiped off for 21 consecutive days. This was indicated by the TEWL readings that were significantly increased compared to Vehicle-treated sites and were similar to the TAZORAC® gel treated sites. TAZORAC® gel was left on the forehead sites for 5 minute and then wiped off. Exfoliation were less than expected with most all subjects experiencing no irritation or exfoliation for either retinoid containing product. Despite the minimal levels of erythema, significantly more erythema was observed on the cheek test sites than the forehead test sites.

TABLE 11

Mean total exfoliation score:

| Product | Example 1 composition Forehead | TAZORAC® gel Cheeks | Vehicle Forehead | Untreated Cheeks |
|---|---|---|---|---|
| Mean total score | 2.2 | 1.7 | 1 | 0.2 |
| Standard deviation | 7.3 | 6.6 | 2.2 | 0.5 |
| p value vs Vehicle* | 0.445 | 0.624 | | |

*p-value from Student's t-test.

TABLE 12

Transepidermal water loss score

| | TAZORAC® gel | | Example 1 composition | | Vehicle composition | | Untreated | |
|---|---|---|---|---|---|---|---|---|
| Day | Mean | SD | Mean | SD | Mean | SD | Mean | SD |
| 1 | 18.2 | 3.3 | 18.3 | 3.5 | 17.1 | 3.4 | 17.1 | 3.4 |
| 2 | 18.3 | 4.6 | 18.7 | 4.5 | 17.9 | 4 | 17.2 | 4.4 |
| 3 | 21.0 | 4.4 | 22.7 | 6.8 | 19.9 | 4.6 | 19.9 | 5 |
| 4 | 19.8 | 4.4 | 23.1 | 8.3 | 20.1 | 5.7 | 19.8 | 4.9 |

TABLE 12-continued

Transepidermal water loss score

| | TAZORAC ® gel | | Example 1 composition | | Vehicle composition | | Untreated | |
|---|---|---|---|---|---|---|---|---|
| Day | Mean | SD | Mean | SD | Mean | SD | Mean | SD |
| 5 | 23.2 | 7.2 | 25 | 14.3 | 22.4 | 6.8 | 21.6 | 6.1 |
| 6 | 24.7 | 10.3 | 24.6 | 9.3 | 21.6 | 4.3 | 20.1 | 4.5 |
| 7 | 24.9 | 5.5 | 30 | 12 | 22.9 | 3.8 | 22.2 | 4.7 |
| 8 | 26.1 | 8.8 | 30.9 | 10.8 | 22.8 | 3.3 | 21 | 3.3 |
| 9 | 25.3 | 6.0 | 28.7 | 9.1 | 22.2 | 4.1 | 21 | 3.9 |
| 10 | 25.9 | 7.3 | 29.7 | 8 | 23 | 4.6 | 20.8 | 4.4 |
| 11 | 25.0 | 7.3 | 28.2 | 8.6 | 22.6 | 3.4 | 20.7 | 4.4 |
| 12 | 24.4 | 7.5 | 26.9 | 7.6 | 21.9 | 3.6 | 20.2 | 4.6 |
| 13 | 27.6 | 8.7 | 31.4 | 10.7 | 24.5 | 4.5 | 23.6 | 5.4 |
| 14 | 26.2 | 9.8 | 28.9 | 6.2 | 22.9 | 4.1 | 21.4 | 3.7 |
| 15 | 29.2 | 12.9 | 32 | 8.8 | 25.8 | 6.2 | 23.7 | 5.6 |
| 16 | 26.3 | 9.6 | 31.5 | 10.6 | 22.8 | 4.4 | 21.7 | 4 |
| 17 | 23.7 | 6.4 | 27.4 | 6.2 | 21.9 | 3.8 | 20.6 | 4.3 |
| 18 | 27.0 | 14.7 | 27.9 | 8.9 | 21.8 | 3.8 | 20.7 | 4.3 |
| 19 | 26.2 | 9.6 | 28.9 | 9.6 | 21.3 | 3.4 | 20.3 | 4 |
| 20 | 25.5 | 8.2 | 27.1 | 9.2 | 21.4 | 3.6 | 20.9 | 4.6 |
| 21 | 25.5 | 8.3 | 25.9 | 8.8 | 22.1 | 4.2 | 20.1 | 3.5 |
| 22 | 23.8 | 8.5 | 25.9 | 9.6 | 19.5 | 4.1 | 18.5 | 3.2 |

Throughout this document, various references are mentioned. All such references are incorporated herein by reference.

What is claimed is:

1. A topical lotion composition, comprising:
   a) a retinoid compound;
   b) an oil phase comprising one or more water immiscible substances;
   c) a hydrophilic phase comprising water;
   d) a thickener;
   e) one or more dermatologically acceptable excipient; and
   f) one or more surfactants in the range from about 0.01% w/w to about 10% w/w of the total weight of the composition;
   wherein the composition is free of propellant, and wherein the composition has pH from about 4 to about 7; wherein the composition excludes peanut oil.

2. The topical composition of claim 1, wherein said retinoid compound is selected from tretinoin, isotretinoin, acitretin, tazarotene, and adapalene.

3. The topical composition of claim 1, wherein the retinoid compound is tazarotene.

4. The composition of claim 1, wherein the retinoid compound is tretinoin.

5. The topical composition of claim 1, wherein the retinoid compound is suspended in the composition.

6. The topical composition of claim 1, wherein the particle size of the retinoid compound is less than about 50 microns.

7. The topical composition of claim 1, wherein the composition comprises at least about 60% w/w water based on the total weight of the composition.

8. The topical composition of claim 1, wherein D90 globule size of oil phase is at least 2 microns and less than about 50 microns.

9. The topical composition of claim 1, wherein the thickener is selected from carbomers, polyvinyl pyrrolidone, locust gum, polyvinyl alcohol, cross-linked polyacrylate polymer, guar gum, locust bean gum, polysaccharides, cellulose polymers and any combinations thereof.

10. The topical composition of claim 9, wherein the thickener comprises a carbomer.

11. A method of treating the skin disorder comprising: administering the topical composition of claim 1, to a patient in need thereof, wherein the skin disorder is selected from acne vulgaris, rosacea, atopic dermatitis, skin wrinkles, facial mottle, hyperpigmentation, hypopigmentation, photo aging, papule, pustule, psoriasis, nodulocystic acne lesion and lentigo.

12. A topical lotion composition comprising:
   a) tretinoin or a pharmaceutically acceptable salt thereof;
   b) at least one thickener comprising carbomer;
   c) at least one preservative selected from the group consisting of benzyl alcohol, methylparaben, and combinations thereof;
   d) an antioxidant comprising butylated hydroxytoluene;
   e) a moisturizer comprising glycerin;
   f) an emollient comprising mineral oil;
   g) a pH adjusting agent comprising trolamine;
   h) water; and
   i) one or more surfactants in the range from about 0.01% w/w to about 10% w/w of the total weight of the composition, wherein the one or more surfactants have a hydrophilic/lipophilic balance (HLB) of more than 10, and wherein the composition excludes surfactants selected from cetyl alcohol and stearyl alcohol;
   wherein the composition is free of propellant, and wherein the composition has pH from about 4 to about 7.

13. The topical composition of claim 12, wherein the retinoid compound is suspended in the composition.

14. The topical composition of claim 12, wherein the particle size of the retinoid compound is less than about 50 microns.

15. The topical composition of claim 12, wherein the composition comprises at least about 60% w/w water based on the total weight of the composition.

16. The topical composition of claim 12, wherein D90 globule size of oil phase is at least 2 microns and less than about 50 microns.

17. The topical composition of claim 12, wherein the thickener is the range of from 0.01% to 2%.

18. The topical composition of claim 12, wherein the composition has viscosity in the range of from about 1000 cps to about 50,000 cps, when measured by Brookfield DV-II pro Viscometer with low viscosity spindle no. 4 at 20 rpm.

19. A method of treating the skin disorder comprising: administering the topical composition of claim 12, to a patient in need thereof, wherein the skin disorder is selected from acne vulgaris, rosacea, atopic dermatitis, skin wrinkles, facial mottle, hyperpigmentation, hypopigmentation, photo aging, papule, pustule, psoriasis, nodulocystic acne lesion and lentigo.

20. The topical composition of claim 1, wherein the thickener is the range of from 0.01% to 2%.

21. A topical lotion composition comprising:
   a) a retinoid compound;
   b) an oil phase comprising one or more water immiscible substances;
   c) a hydrophilic phase comprising water;
   d) a thickener; and
   e) one or more dermatologically acceptable excipient;
   wherein the composition is free of propellant;
   wherein the thickener is selected from carbomers, polyvinyl pyrrolidone, locust gum, polyvinyl alcohol, cross-linked polyacrylate polymer, guar gum, locust bean gum, polysaccharides, cellulose polymers and any combinations thereof;
   wherein the composition excludes peanut oil; and wherein a substantial amount of retinoid compound is in hydrophilic phase.

22. A topical lotion composition comprising:
a) tazarotene or a pharmaceutically acceptable salt thereof;
b) at least one thickener comprising carbomer;
c) at least one preservative selected from the group consisting of, methylparaben, propylparaben, and combinations thereof;
d) a chelating agent;
e) an emollient comprising mineral oil;
f) a pH adjusting agent; and
g) water;
wherein the composition is free of propellant;
wherein the composition excludes peanut oil; and
wherein a substantial amount of retinoid compound is in hydrophilic phase.

23. The topical composition of claim 22, wherein the thickener is the range of from 0.01% to 2%.

24. The composition of claim 22, wherein the pH adjusting agent comprises sodium hydroxide.

25. The composition of claim 22, and further comprising one or more surfactants hydrophilic/lipophilic balance (HLB) of more than 10, and wherein the composition excludes surfactants selected from cetyl alcohol and stearyl alcohol.

26. The composition of claim 1, and further comprising at least one preservative selected from the group consisting of benzyl alcohol, methylparaben, propylparaben, and mixtures thereof.

27. The composition of claim 1, and further comprising a preservative comprising methylparaben.

28. The composition of claim 1, and further comprising an emollient.

29. The composition of claim 28, wherein the emollient comprises mineral oil.

30. The composition of claim 1, and wherein the one or more surfactants have a hydrophilic/lipophilic balance (HLB) of more than 10, and wherein the composition excludes surfactants selected from cetyl alcohol and stearyl alcohol.

31. The composition of claim 12, and further comprising an emollient.

32. The composition of claim 31, wherein the emollient comprises mineral oil.

33. The composition of claim 12, wherein the composition excludes peanut oil.

34. The composition of claim 21, and further comprising at least one preservative selected from the group consisting of benzyl alcohol, methylparaben, propylparaben, and mixtures thereof.

35. The composition of claim 21, and further comprising a preservative comprising methylparaben.

36. The composition of claim 21, and further comprising an emollient.

37. The composition of claim 36, wherein the emollient comprises mineral oil.

38. The composition of claim 21, and further comprising one or more surfactants having a hydrophilic/lipophilic balance (HLB) of more than 10, and wherein the composition excludes surfactants selected from cetyl alcohol and stearyl alcohol.

39. The composition of claim 1, wherein the composition has a viscosity in the range of from about 1000 cps to about 50,000 cps, when measured by Brookfield DV-II pro Viscometer with low viscosity spindle no. 4 at 20 rpm.

40. The composition of claim 21, wherein the composition has a viscosity in the range of from about 1000 cps to about 50,000 cps, when measured by Brookfield DV-II pro Viscometer with low viscosity spindle no. 4 at 20 rpm.

41. The composition of claim 22, wherein the composition has a viscosity in the range of from about 1000 cps to about 50,000 cps, when measured by Brookfield DV-II pro Viscometer with low viscosity spindle no. 4 at 20 rpm.

* * * * *